(12) United States Patent  
Gharpure et al.

(10) Patent No.: US 8,321,364 B1
(45) Date of Patent: Nov. 27, 2012

(54) METHOD AND SYSTEM FOR INCLUDING ROBOTS INTO SOCIAL NETWORKS

(75) Inventors: Chaitanya Gharpure, Sunnyvale, CA (US); Ryan Hickman, Mountain View, CA (US)

(73) Assignee: Google Inc., Mountain View, CA (US)

(*) Notice: Subject to any disclaimer, the term of this patent is extended or adjusted under 35 U.S.C. 154(b) by 0 days.

(21) Appl. No.: 13/471,149

(22) Filed: May 14, 2012

Related U.S. Application Data

(60) Provisional application No. 61/596,608, filed on Feb. 8, 2012.

(51) Int. Cl.
*G06F 17/00* (2006.01)
(52) U.S. Cl. .......................................................... 706/45
(58) Field of Classification Search ........................ None
See application file for complete search history.

(56) References Cited

U.S. PATENT DOCUMENTS

| 2010/0241693 | A1 | 9/2010 | Ando et al. | |
| 2011/0004519 | A1* | 1/2011 | Aleong et al. | 705/14.53 |
| 2011/0131493 | A1* | 6/2011 | Dahl | 715/716 |

FOREIGN PATENT DOCUMENTS

WO 2010093995 8/2010

OTHER PUBLICATIONS

Raffle, Hayes, et al., Pokaboo: A Networked Toy for Distance Communication and Play, Jun. 2011.

* cited by examiner

*Primary Examiner* — Jeffrey A. Gaffin
*Assistant Examiner* — Paulinho E Smith
(74) *Attorney, Agent, or Firm* — McDonnell Boehnen Hulbert & Berghoff LLP

(57) ABSTRACT

Examples disclose a method and system for including robots into social networks. The method may be executable to receiving information associated with a first party, wherein the first party is connected to a second party by a social-network. Based on the received information, the method may be executable to query a behavioral database to obtain a behavioral expectation associated with the first party and to compare the behavioral expectation associated with the first party to a stored behavioral expectation associated with the second party. Based on the comparing, the method may be executable to modify the stored behavioral expectation associated with the second party based on the behavioral expectation associated with the first party and provide instructions, which are executable to perform an action associated with the modified behavioral expectation, to a device associated with the second party.

20 Claims, 9 Drawing Sheets

METHOD AND SYSTEM FOR INCLUDING ROBOTS INTO SOCIAL NETWORKS

CROSS-REFERENCE TO RELATED APPLICATION

This patent application claims priority to U.S. Patent Application No. 61/596,608 filed on Feb. 8, 2012, the contents of which are entirely incorporated herein by reference, as if fully set forth in this application.

BACKGROUND

Cloud computing refers to provision of computational resources via a computer network. In a traditional model of computing, both data and software are fully contained on a user's computer. In cloud computing, however, the user's computer may contain relatively little software or data (perhaps a minimal operating system and web browser, for example), and may serve as a display terminal for processes occurring on a network of computers. A common shorthand provided for a cloud computing service (or even an aggregation of existing cloud services) is "the cloud".

Cloud computing has been referred to as "client-server computing", however, there may be distinctions between general cloud computing and client-server computing. For example, client-server computing may include a distributed application structure that partitions tasks or workloads between providers of a resource or service (e.g., servers), and service requesters (e.g., clients). Client-server computing generally involves a one-to-one relationship between the server and the client, whereas cloud computing includes generic services that can be accessed by generic clients (e.g., a one-to-one relationship or connection may not be required). Thus, cloud computing generally includes client-server computing, and additional services and functionality.

Cloud computing may free users from certain hardware and software installation and maintenance tasks through use of simpler hardware on the user's computer that accesses a vast network of computing resources (e.g., processors, hard drives, etc.). Sharing of resources may reduce cost to individuals. Thus, any computer connected to the cloud may be connected to the same pool of computing power, applications, and files. Users can store and access personal files such as music, pictures, videos, and bookmarks or play games or use productivity applications on a remote server rather than physically carrying around a storage medium, such as a DVD or thumb drive.

In one example, a user may open a browser and connect to a host of web servers that run user interface software for collecting commands from the user and interpreting the commands into commands on the servers. The servers may handle the computing, and can either store or retrieve information from database servers or file servers and display an updated page to the user. Through "cloud computing", data across multiple servers can be synchronized around the world allowing for collaborative work on one file or project by multiple users around the world, for example.

SUMMARY

The present application discloses, inter alia, methods and systems for robot cloud computing.

Any of the methods described herein may be provided in a form of instructions stored on a non-transitory, computer readable medium, that when executed by a computing device, cause the computing device to perform functions of the method. Further examples may also include articles of manufacture including tangible computer-readable media that have computer-readable instructions encoded thereon, and the instructions may comprise instructions to perform functions of the methods described herein.

The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage medium.

In addition, circuitry may be provided that is wired to perform logical functions in any processes or methods described herein.

In still further examples, many types of devices may be used or configured to perform logical functions in any of the processes or methods described herein.

In yet further examples, many types of devices may be used or configured as means for performing functions of any of the methods described herein (or any portions of the methods described herein).

For example, a method may be performed by a computing system having a processor and memory. The method may be executable to receive information associated with a first party, wherein the first party is connected to a second party by a social-network, wherein the social-network comprises a network of parties, including the first party and the second party, that are related via one or more relationships, the one or more relationships indicating a type of connection between the first party and the second party. Based on the received information, the method may be executable to query a behavioral database to obtain a behavioral expectation associated with the first party, wherein the behavioral expectation indicates an action associated with the first party. The method may be further executable to compare the behavioral expectation associated with the first party to a stored behavioral expectation associated with the second party to determine if the behavioral expectation associated with the first party differs from the stored behavioral expectation associated with the second party. Based on the comparison, the method may be executable to modify the stored behavioral expectation associated with the second party based on the behavioral expectation associated with the first party and to provide instructions, which are executable to perform an action associated with the modified behavioral expectation, to a device associated with the second party.

In another example, a system may include a first party device, wherein the first party device includes a robotic device having a mechanical actuator. The system may further include a computing system including a computer-readable memory and program instructions stored on the computer-readable memory and executable by at least one processor to cause the computing system to perform a number of functions. For example, a function may include determining if the first party device is associated with a second party device by a social-network, wherein the social-network comprises a network of parties, including a first party associated with the first party device and a second party associated with the second party device, wherein the first party and the second party are related via one or more relationships, the one or more relationships indicating a type of connection between the first party and the second party. Moreover, based on the received information, a function may include querying a behavioral database to obtain a behavioral expectation associated with the second party, wherein the behavioral expectation indicates an action associated with the second party. A function may further include a comparison of the behavioral expectation associated with the second party to a stored behavioral expectation associated with the first party. In response to the comparison, a function may include modifying the stored behavioral expectation associated with the first party based on the behavioral expectation associated with the second party.

In yet another example, a computer-readable memory may have stored thereon instructions executable by a computing device having at least one processor to cause the computing device to perform a number of functions. A function may include receiving information associated with a first party, wherein the first party is connected to a second party by a social-network, wherein the social-network comprises a network of parties, including the first party and the second party, that are related via one or more relationships, the one or more relationships indicating a type of connection between the first party and the second party. Based on the received information, a function may query a behavioral database to obtain a behavioral expectation associated with the first party, wherein the behavioral expectation indicates an action associated with the first party. A function may compare the behavioral expectation associated with the first party to a stored behavioral expectation associated with the second party. Responsive to the comparing, a function may modify the stored behavioral expectation associated with the second party based on the behavioral expectation associated with the first party and providing instructions, which are executable to perform an action associated with the modified behavioral expectation, to a device associated with the second party.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION

Figure 1:
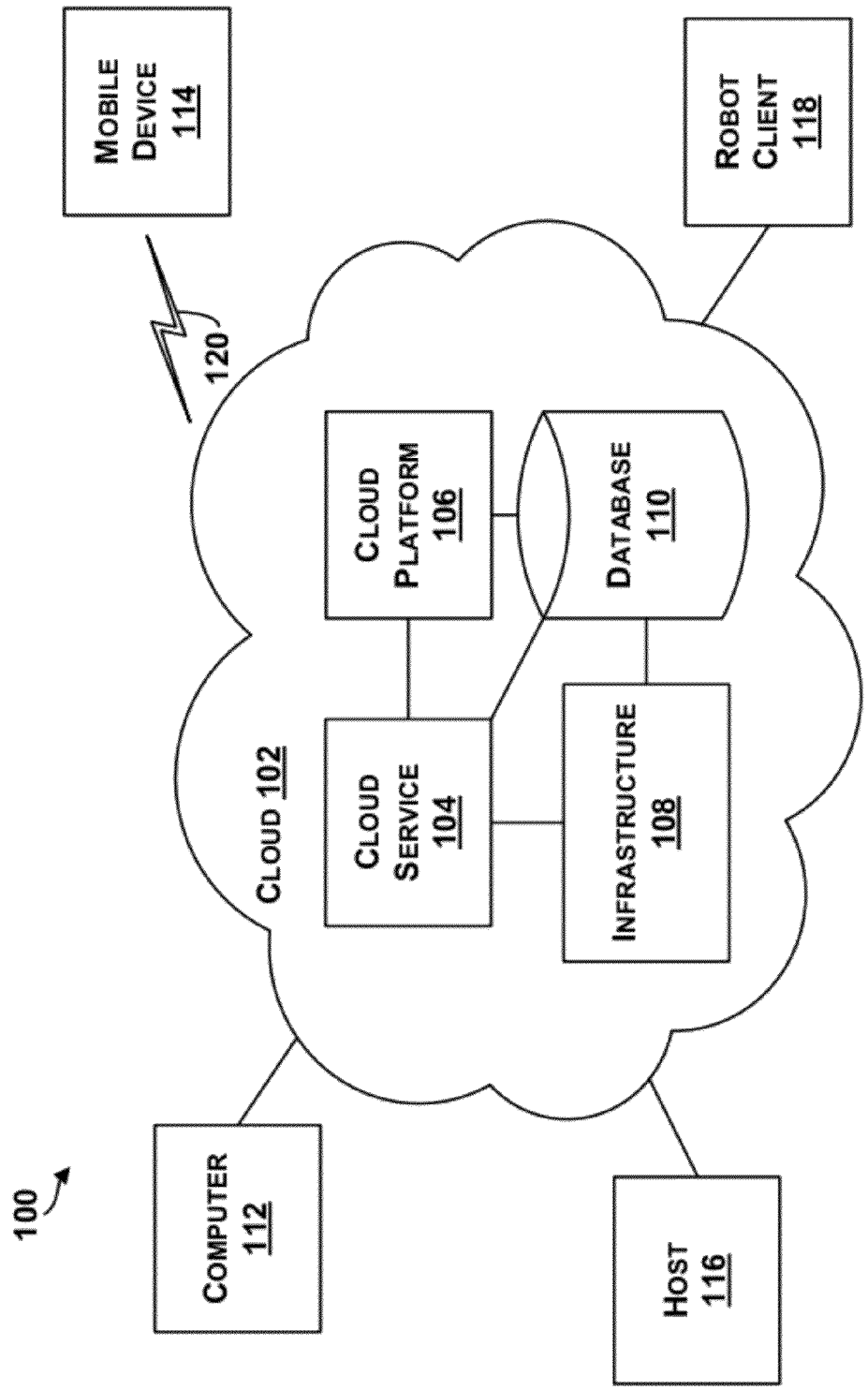
FIG. 1 is an example system for cloud-based computing.

In the following detailed description, reference is made to the accompanying figures. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

1. Cloud Computing

Cloud computing may generally refer to the provision of computational resources via a computer network and, in particular, may refer to networked computer architectures in which application execution and storage may be divided, to some extent, between client and server devices. A common shorthand provided for a cloud computing service (or even an aggregation of existing cloud services) is "the cloud".

General cloud computing may be distinct from client-server computing. For example, client-server computing may include a distributed application structure that partitions tasks or workloads between providers of a resource or service (e.g., servers), and service requesters (e.g., clients). Client-server computing may generally involve a one-to-one relationship between the server and the client, whereas cloud computing may include generic services that can be accessed by generic clients (e.g., a one-to-one relationship or connection may not be required). Thus, cloud computing generally includes client-server computing, and additional services and functionality.

Cloud computing may free users from certain hardware and software installation and maintenance tasks through use of simpler hardware on the user's computer that accesses a vast network of computing resources (e.g., processors, hard drives, etc.). Sharing of resources may reduce cost to individuals. Thus, any computer connected to the cloud may be connected to the same pool of computing power, applications, and files. Users can store and access personal files such as music, pictures, videos, and bookmarks or play games or use productivity applications on a remote server rather than physically carrying around a storage medium, such as a DVD or thumb drive.

In one example, a user may open a browser and connect to a host of web servers that run user interface software that collect commands from the user and interpret the commands into commands on the servers. The servers may handle the computing, and can either store or retrieve information from database servers or file servers and display an updated page to the user. Through "cloud computing", data across multiple servers can be synchronized around the world allowing for collaborative work on one file or project, from multiple users around the world, for example.

Within examples, cloud-based computing may be used to allow a robot to communicate with another robot or computing device. A robot may be any device that has a computing ability and interacts with its surroundings with an actuation capability (e.g., electromechanical capabilities). A client device may be configured as a robot including various sensors and devices in the forms of modules, and different modules may be added or removed from robot depending on requirements. In some examples, a robot may be configured to receive a second device, such as a mobile phone, that may be configured to function as an accessory or a "brain" of the robot.

2. Cloud Computing Architecture

Referring now to the figures, FIG. 1 is an example system 100 for cloud-based computing. Cloud-based computing generally refers to networked computer architectures in which application execution and storage may be divided, to some extent, between client and server devices. A "cloud" may refer to a service or a group of services accessible over a network (e.g., Internet) by client and server devices, for example.

In one example, any computer connected to the cloud may be connected to the same pool of computing power, applications, and files. Thus, cloud computing enables a shared pool of configurable computing resources (e.g., networks, servers, storage, applications, and services) that can be provisioned and released with minimal management effort or service provider interaction. Users can store and access personal files such as music, pictures, videos, and bookmarks or play games or use productivity applications on a remote server rather than physically carrying around a storage medium.

As an example, in contrast to a predominately client-based or server-based application, a cloud-based application may store copies of data and/or executable program logic at remote server devices, while allowing client devices to download at least some of this data and program logic as needed for execution at the client devices. In some examples, downloaded data and program logic can be tailored to capabilities of specific client devices (e.g., a personal computer, tablet, or mobile phone, or robot) accessing the cloud based application. In addition, dividing application execution and storage between the client and server devices allows more processing to be performed by the server devices taking advantage of server devices processing power and capability, for example.

Cloud-based computing can also refer to distributed computing architectures in which data and program logic for a cloud-based application are shared between one or more client devices and/or server devices on a near real-time basis. Parts of this data and program logic may be dynamically delivered, as needed or otherwise, to various clients accessing the cloud-based application. Details of the architecture may be transparent to users of client devices. Thus, a PC user or robot client device accessing a cloud-based application may not be aware that the PC or robot downloads program logic and/or data from the server devices, or that the PC or robot offloads processing or storage functions to the server devices, for example.

In FIG. 1, a cloud 102 includes a cloud service 104, a cloud platform 106, a cloud infrastructure 108, and a database 110. The cloud 102 may include more of fewer components, and each of the cloud service 104, the cloud platform 106, the cloud infrastructure 108, and the database 110 may comprise multiple elements as well. Thus, one or more of the described functions of the system 100 may be divided up into additional functional or physical components, or combined into fewer functional or physical components. In some further examples, additional functional and/or physical components may be added to the examples illustrated by FIG. 1. Delivery of cloud computing may involve multiple cloud components communicating with each other over application programming interfaces, such as web services and three-tier architectures, for example.

The cloud 102 may represent a networked computer architecture, and in one example, the cloud service 104 represents a queue for handling requests from client devices. The cloud platform 106 may include a frontend of the cloud and may be coupled to the cloud service 104 to perform functions to interact with client devices. The cloud platform 106 may include applications used to access the cloud 102 via a user interface, such as a web browser. The cloud infrastructure 108 may include service application of billing components of the cloud 102, and thus, may interact with the cloud service 104. The database 110 may represent storage capabilities by the cloud 102, and thus, may be accessed by any of the cloud service 104, the cloud platform 106, and/or the infrastructure 108.

The system 100 may include a number of client devices coupled to or configured to be capable of communicating with components of the cloud 102. For example, a computer 112, a mobile device 114, a host 116, and a robot client 118 are shown coupled to the cloud 102. Of course, more or fewer client devices may be coupled to the cloud 102. In addition, different types of client devices may be coupled to the cloud 102. For example, any of the client devices may generally comprise a display system, memory, and a processor.

The computer 112 may be any type of computing device (e.g., PC, laptop computer, etc.), and the mobile device 114 may be any type of mobile computing device (e.g., laptop, mobile telephone, cellular telephone, etc.).

The host 116 may be any type of computing device or transmitter including a laptop computer, a mobile telephone, etc., that is configured to transmit data to the cloud 102.

The robot client 118 may comprise any computing device that has connection abilities to the cloud 102 and that has an actuation capability (e.g., electromechanical capabilities). A robot may further be a combination of computing devices. In some examples, the robot 118 may collect data and upload the data to the cloud 102. The cloud 102 may be configured to perform calculations or analysis on the data and return processed data to the robot client 118. In some examples, as shown in FIG. 1, the cloud 102 may include a computer that is not co-located with the robot client 118. In other examples, the robot client 118 may send data to a second client (e.g., computer 112) for processing.

Any of the client devices may include additional components. For example, the robot client 118 may include one or more sensors, such as a gyroscope or an accelerometer to measure movement of the robot client 118. Other sensors may further include any of Global Positioning System (GPS) receivers, infrared sensors, optical sensors, biosensors, Radio Frequency identification (RFID) systems, wireless sensors, and/or compasses, among others, for example.

In addition, any of the client devices may include an integrated user-interface (UI) that allows a user to interact with the device. For example, the robot client 118 may include various buttons and/or a touchscreen interface that allow a user to provide input. As another example, the robot client device 118 may include a microphone configured to receive voice commands from a user. Furthermore, the robot client 118 may include one or more interfaces that allow various types of user-interface devices to be connected to the robot client 118.

In FIG. 1, communication links between client devices and the cloud 102 may include wired connections, such as a serial or parallel bus. Communication links may also be wireless links, such as link 120, which may include Bluetooth, IEEE 802.11 (IEEE 802.11 may refer to IEEE 802.11-2007, IEEE 802.11n-2009, or any other IEEE 802.11 revision), or other wireless based communication links.

In other examples, the system 100 may include access points through which the client devices may communicate with the cloud 102. Access points may take various forms, for example, an access point may take the form of a wireless access point (WAP) or wireless router. As another example, if a client device connects using a cellular air-interface protocol, such as a CDMA or GSM protocol, an access point may be a base station in a cellular network that provides Internet connectivity via the cellular network.

As such, the client devices may include a wired or wireless network interface through which the client devices can connect to the cloud 102 (or access points). As an example, the client devices may be configured to use one or more protocols such as 802.11, 802.16 (WiMAX), LTE, GSM, GPRS, CDMA, EV-DO, and/or HSPDA, among others. Furthermore, the client devices may be configured to use multiple wired and/or wireless protocols, such as "3G" or "4G" data connectivity using a cellular communication protocol (e.g., CDMA, GSM, or WiMAX, as well as for "WiFi" connectivity using 802.11). Other examples are also possible.

3. Example Robot Architecture

Figure 2A:
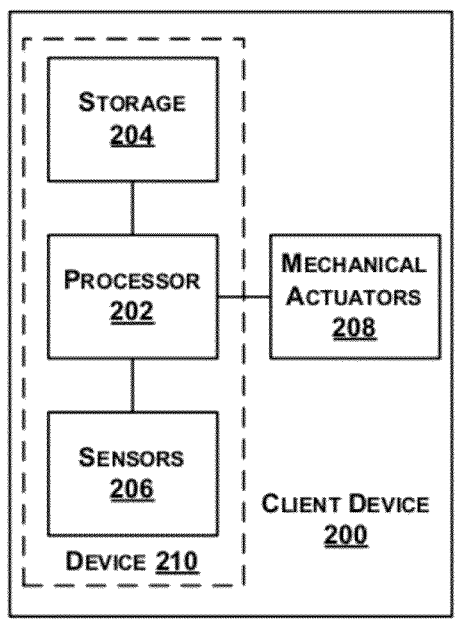
FIG. 2A illustrates an example client device.

FIG. 2A illustrates an example client device 200. In one example, the client device 200 is configured as a robot. In some examples, a robot may contain computer hardware, such as a processor 202, memory or storage 204, and sensors 206. For example, a robot controller (e.g., processor 202, computing system, and sensors 206) may all be custom designed for a specific robot. The robot may have a link by which the link can access cloud servers (as shown in FIG. 1). A wired link may include, for example, a parallel bus or a serial bus such as a Universal Serial Bus (USB). A wireless link may include, for example, Bluetooth, IEEE 802.11, Cellular (such as GSM, CDMA, UMTS, EV-DO, WiMAX, or LTE), or Zigbee, among other possibilities.

In one example, the storage 204 may be used for compiling data from various sensors 206 of the robot and storing program instructions. The processor 202 may be coupled to the storage 204 and may be configured to control the robot based on the program instructions. The processor 202 may also be able to interpret data from the various sensors 206 on the robot. Example sensors may include, smoke sensors, light sensors, radio sensors, infrared sensors, microphones, speakers, gyroscopes, accelerometer, a camera, radar, capacitive sensors and touch sensors, etc.

The client device 200 may also have components or devices that allow the client device 200 to interact with its environment. For example, the client device 200 may have mechanical actuators 208, such as motors, wheels, movable arms, etc., that enable the client device 200 to move or interact with the environment.

In some examples, various sensors and devices on the client device 200 may be modules. Different modules may be added or removed from a client device 200 depending on requirements. For example, in a low power situation, a robot may have fewer modules to reduce power usages. However, additional sensors may be added as needed. To increase an amount of data a robot may be able to collect, additional sensors may be added, for example.

In some example, the client device 200 may be configured to receive a device, such as device 210, that includes the processor 202, the storage 204, and the sensors 206. For example, the client device 200 may be a robot that have a number of mechanical actuators (e.g., a movable base), and the robot may be configured to receive a mobile telephone to function as the "brains" or control components of the robot. The device 210 may be considered a module of the robot. The device 210 may be physically attached to the robot. For example, a mobile phone may sit on a robot's "chest" and form an interactive display. The device 210 may provide a robot with sensors, a wireless link, and processing capabilities, for example. The device 210 may allow a user to download new routines for his or her robot from the cloud. For example, a laundry folding routine may be stored on the cloud, and a user may be able to select this routine using a mobile phone to download the routine from the cloud, and when the mobile phone is placed into or coupled to the robot, the robot would be able to perform the downloaded action.

In some examples, the client device 200 may be coupled to a mobile or cellular telephone to provide additional sensing capabilities. The cellular phone may not be physically attached to the robot, but may be coupled to the robot wirelessly. For example, a low cost robot may omit a direct connection to the internet. This robot may be able to connect to a user's cellular phone via a wireless technology (e.g., Bluetooth) to be able to access the internet. The robot may be able to access various sensors and communication means of the cellular phone. The robot may not need as many sensors to be physically provided on the robot, however, the robot may be able to keep the same or similar functionality.

Thus, the client device 200 may include mechanical robot features, and may be configured to receive the device 210 (e.g., a mobile phone), which can provide additional peripheral components to the device 200, such as any of an accelerometer, gyroscope, compass, GPS, camera, WiFi connection, a touch screen, etc., that are included within the device 210.

Figure 2B:
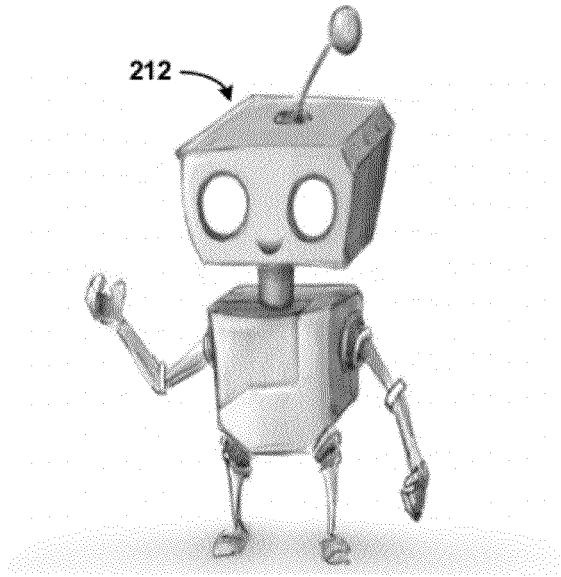
FIG. 2B illustrates a graphical example of a robot.

FIG. 2B illustrates a graphical example of a robot 212. In FIG. 2B, the robot 212 is shown as a mechanical form of a person including arms, legs, and a head. The robot 212 may be configured to receive any number of modules or components, such as a mobile phone, which may be configured to operate the robot. In this example, a device (e.g., robot 212) can be attached to a mobile phone (e.g., device 210) to provide the mechanical robot 212 with functionality enabling the robot 212 to communicate with the cloud to cause operation/functions of the robot 212. Other types of devices that have connectivity to the Internet can be coupled to robot 212 to provide additional functions on the robot 212. Thus, the device 210 may be separate from the robot 212 and can be attached or coupled to the robot 212.

In one example, the robot 212 may be a toy with only limited mechanical functionality, and by connecting device 210 to the robot 212, the toy robot 212 may now be capable of performing a number of functions with the aid of the device 210 and/or the cloud. In this manner, the robot 212 (or components of a robot) can be attached to a mobile phone to transform the mobile phone into a robot (e.g., with legs/arms) that is connected to a server to cause operation/functions of the robot.

The mountable device 210 may further be configured to maximize runtime usage of the robot 212 (e.g., if the robot 212 could learn what happens to cause the user to turn the toy off or set the toy down, the device 210 may be configured to perform functions to counteract such occurrences).

Figure 2C:
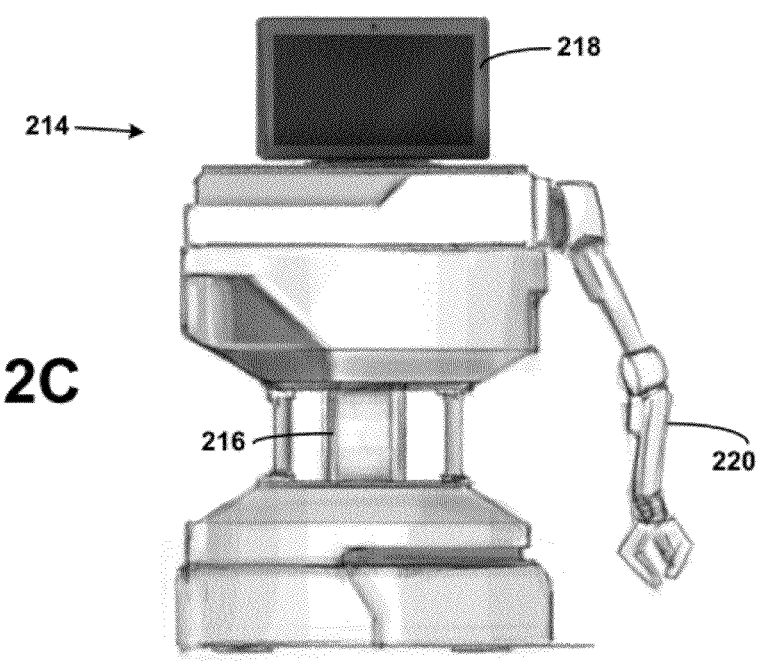
FIG. 2C illustrates another example of a robot.

FIG. 2C illustrates another example of a robot 214. The robot 214 includes a computing device 216, sensors 218, and a mechanical actuator 220. In this example, the computing device 216 may be a laptop computer, which may be coupled to the sensors 218. The sensors 218 may include a camera, infrared projectors, and other motion sensing or vision sensing elements. The mechanical actuator 220 may include a base, wheels, and a motor upon which the computing device 216 and the sensors 218 can be positioned, for example.

Any of the robots illustrated in FIGS. 2A-2C may be configured to operate according to a robot operating system (e.g., an operating system designed for specific functions of the robot). A robot operating system may provide libraries and tools (e.g., hardware abstraction, device drivers, visualizers, message-passing, package management, etc.) to enable robot applications. Examples of robot operating systems include open source software such as ROS (robot operating system), DROS, or ARCOS (advanced robotics control operating system); proprietary software such as the robotic development platform ESRP from Evolution Robotics® and MRDS (Microsoft® Robotics Developer Studio), and other examples also include ROSJAVA. A robot operating system may include publish and subscribe functionality, and may also include functionality to control components of the robot, such as head tracking, base movement (e.g., velocity control, navigation framework), etc.

4. Robot and Cloud Interaction

Figure 3:
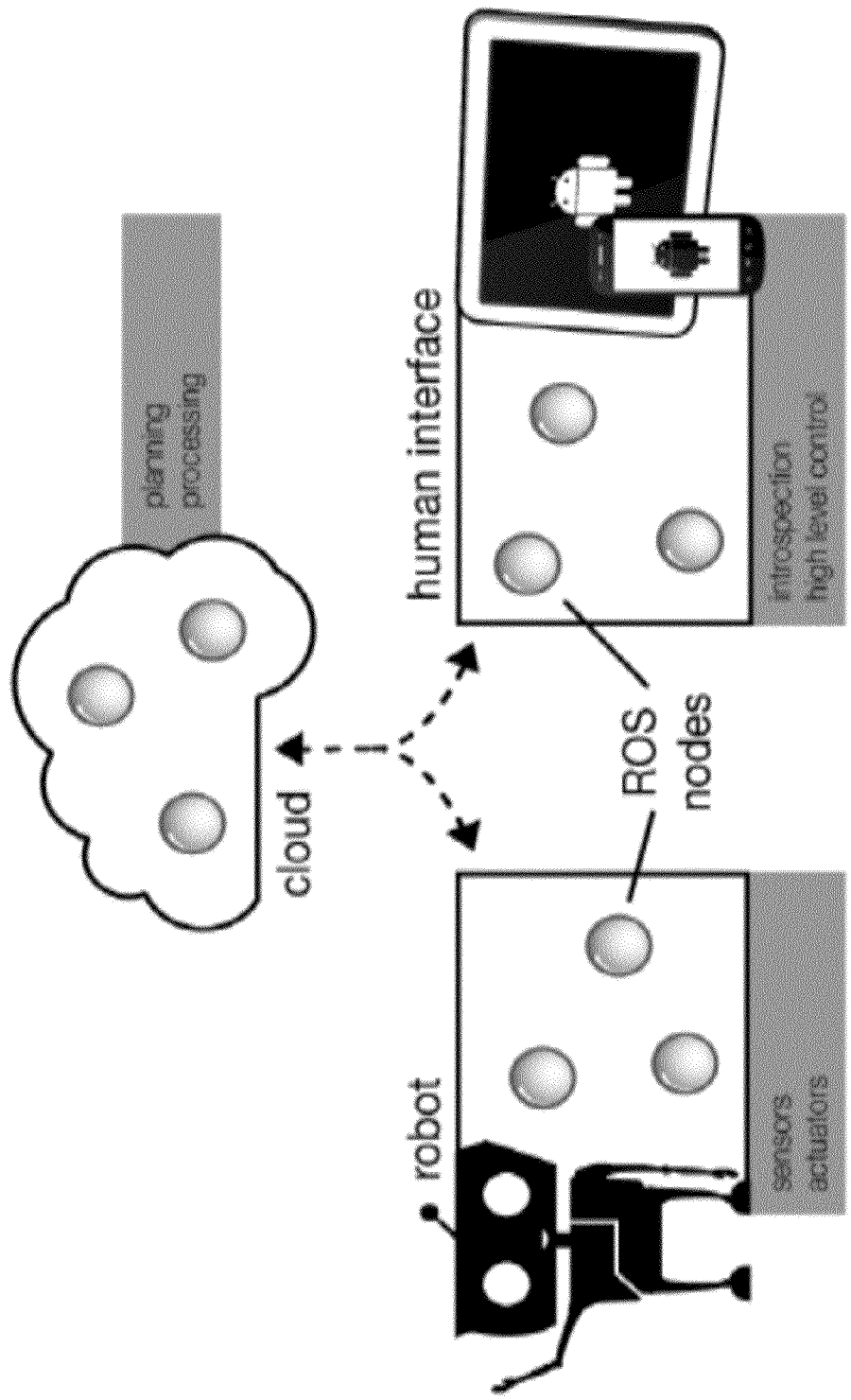
FIG. 3 illustrates an example of a conceptual robot-cloud interaction.

FIG. 3 illustrates an example of a conceptual robot-cloud interaction. A robot, such as a robot described and illustrated in FIG. 2, may connect to a network of computers (e.g., the cloud), and may request data or processing to be performed by the cloud. In one example, the robot may include a number of sensors and mechanical actuators that may generally provide motor control for the robot. Outputs of the sensors, such as camera feeds, vision sensors, etc., may be provided to the cloud, which can process the outputs to enable the robot to perform functions. The cloud may process a camera feed, for example, to determine a location of a robot, perform object recognition, or to indicate a navigation pathway for the robot.

FIG. 3 generally illustrates motor controllers in which each module may conceptually represent a computer or node on the cloud that performs processing using motor controller inputs or data from the robot. FIG. 3 also generally illustrates sensors in which each module may conceptually represent a computer or node on the cloud that performs processing using sensor inputs or data from the robot. FIG. 3 further generally illustrates applications in which each module may conceptually represent a computer or node on the cloud that performs specific functions of a number of applications, e.g., navigation application, mapping application, etc. In addition, FIG. 3 further generally illustrates planning in which each module may conceptually represent a computer or node on the cloud that performs processing for the robot, such as general planning or computing processing.

As shown, any of the modules may be interconnected, and/or may communicate to receive data or instructions from each other so as to provide a specific output or functionality for the robot.

In one example, the robot may send data to a cloud for data processing, and in another example the robot may receive data from the cloud. The data received from the cloud may be in many different forms. The received data may be a processed form of data the robot sent to the cloud. The received data may also come from sources other than the robot. For example, the cloud may have access to other sensors, other robots, and the internet.

Figure 4:
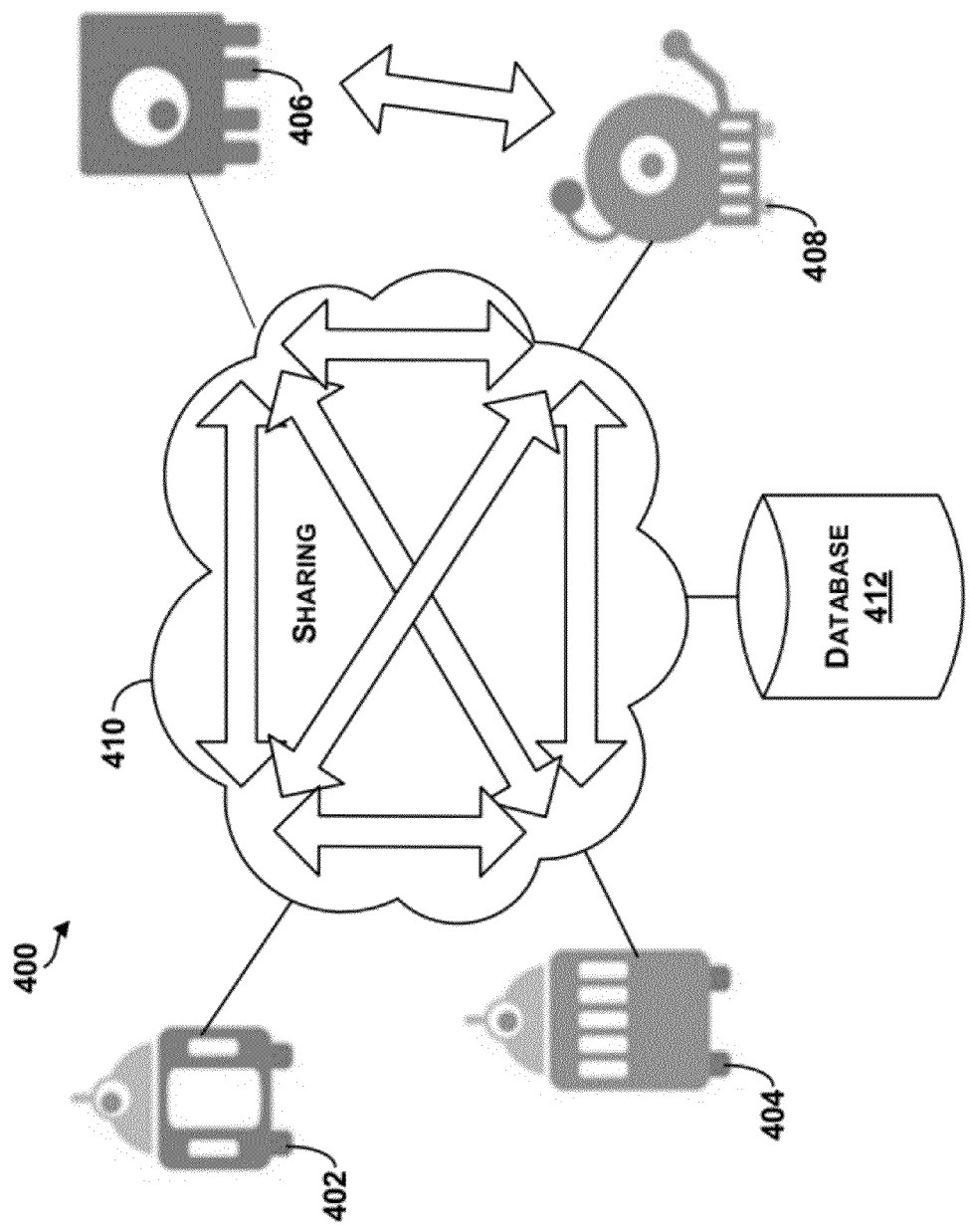
FIG. 4 is an example system in which robots may interact with the cloud and share information with other cloud computing devices.

FIG. 4 is an example system 400 in which robots may interact with the cloud and shares information with other cloud computing devices. The system 400 illustrates robots 402, 404, 406, and 408 (e.g., as conceptual graphical representations) each coupled to a cloud 410. Each robot 402, 404, 406, and 408 may interact with the cloud 410, and may further interact with each other through the cloud 410, or through other access points and possibly directly (e.g., as shown between robots 406 and 408).

The cloud 410 may receive input from several robots. Data from each robot may be complied into a larger data set. For example, the robot 402 may take a picture of an object and upload the picture to the cloud 410. An object recognition program on the cloud 410 may be configured to identify the object in the picture and provide data to all the robots connected to the cloud 410 about the recognized object, as well as possibly about other characteristics (e.g., metadata) of the recognized object, such as a location, size, weight, color, etc. Thus, every robot may be able to know attributes of an object in a photo uploaded by the robot 402.

In one example, the cloud 410 may include, store, or provide access to a database 412 of information related to objects, and the database 412 may be accessible by all the robots 402, 404, 406, and 408. The database 412 may include information identifying objects, and details of the objects (e.g., mass, properties, shape, instructions for use, etc., any detail that may be associated with the object) that can be accessed by the robots 402, 404, 406, 408 to perform object recognition. As an example, information regarding use of an object can include, e.g., such as for a phone, how to pick up a handset, how to answer the phone, location of buttons, how to dial, etc.

In addition, the database 412 may include information about objects that can be used to distinguish objects. For example, the database 412 may include general information regarding an object (e.g., such as a computer), and additionally, information regarding a specific computer (e.g., a model number, details or technical specifications of a specific model, etc.). Each object may include information in the database 412 including an object name, object details, object distinguishing characteristics, etc., or a tuple space for objects that can be accessed. Each object may further include information in the database in an ordered list, for example. In further examples, the database 412 may include a global unique identifier (GUID) for objects identified in the database 412 (e.g., to enable distinguishing between specific objects), and the GUID may be associated with any characteristics or information describing the object. Thus, a robot may be configured to access the database 412 to receive information generally distinguishing objects (e.g., a baseball vs. a computer), and to receive information that may distinguish between specific objects (e.g., two different computers).

The database 412 may be accessible by all robots through the cloud 410 (or alternatively directly accessible by all robots without communication through the cloud 410). The database 412 may thus be a shared knowledge-base stored in the cloud 410. Within examples, the robots 402, 404, 406, 408 may share information through the cloud 410, and may access the database 412. In some examples, the shared database 412 may include information shared across social-networks.

5. Social-Networking

Social-networking technology may be used as a convenient way to connect and foster relationships with friends, family, and business colleagues. In practice, a typical social-networking service may have many members (or "nodes") and may store profile data for each member including data that defines connections or interrelationships between the member and various other members of the service. In particular, the connection data may define for each member one or more social-network groups, each including one or more other members with whom the member is connected. The social-networking service may then allow members to share information, data, content, and the like with other members of their social-network group(s) in a computer implemented, virtual environment. For instance, through interaction with the social-networking service, a member may conveniently receive social-network updates posted by other members with whom the member is connected and may view profile information such as connections of those other members.

Once an account is established with a social-networking service, one or more social-network groups may be created by adding connections to other accounts and organizations. The manner in which these connections are added, however, may vary from social-networking service to social-networking service. For instance, some social-networking services operate in a symmetric manner in which a member may submit a request to "friend" or add to the member's social-network group a connection with a specified party, and the social-networking service may then invite that party to become a connection in the member's social-network group and adds the requested connection if the party accepts the invitation. In other examples, other social-networking services operate in an asymmetric manner in which a member may submit a request to "follow" a specified party, and the social-networking service may then add to the member's social-network group a connection with that party without formally inviting and receiving an acceptance from the party.

6. Example Social Network Architecture

Figure 5:
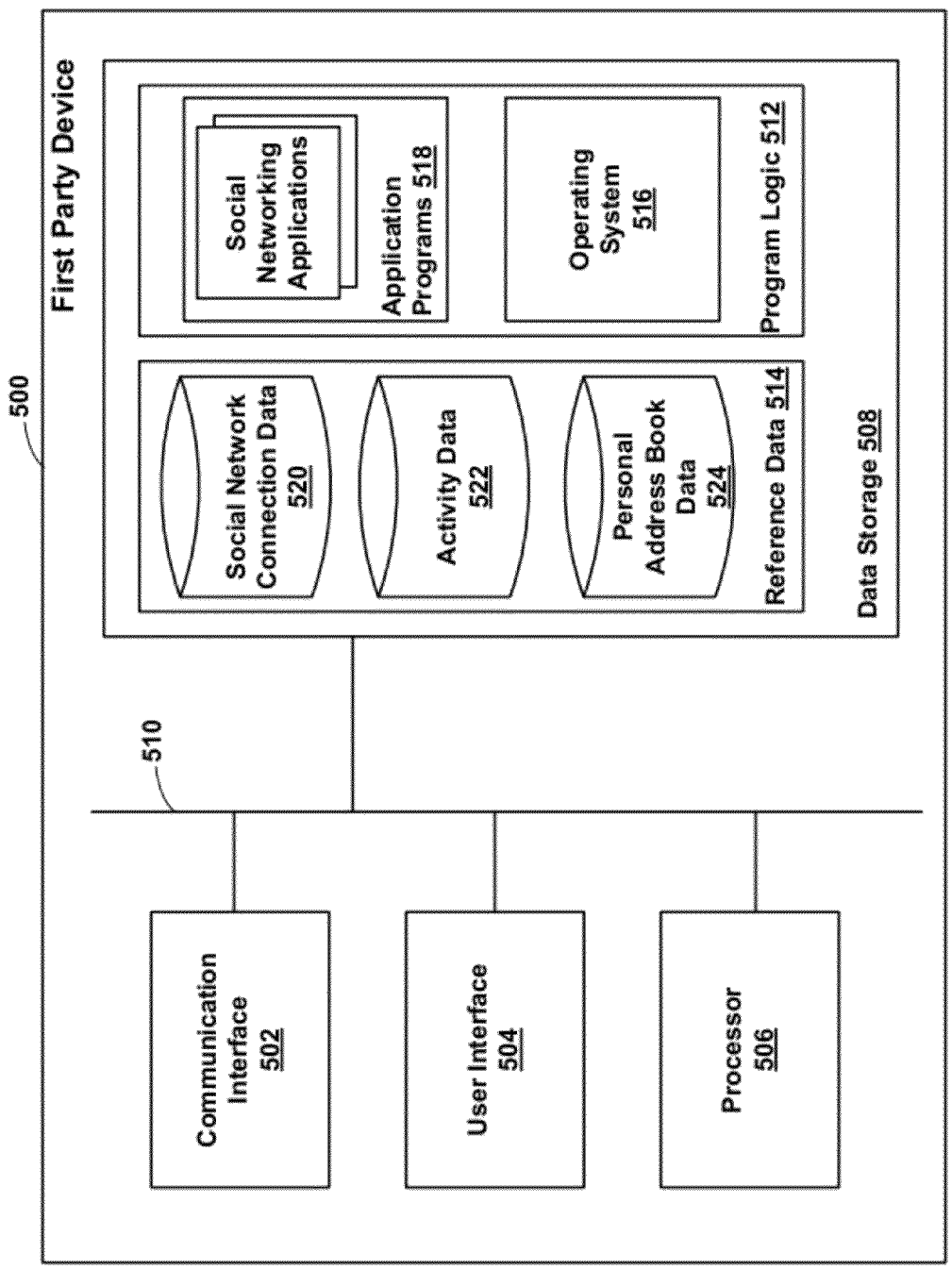
FIG. 5 illustrates a block diagram showing some components of an example first party device.

FIG. 5 illustrates a block diagram showing some of the components of an example first party device 500 that can be used to connect or otherwise communicate with a social network. In practice, some of these components or their functions may be distributed across multiple first party devices. However, the components are shown and described as part of a representative first party device for sake of example. The first party device reference number may be a robot (e.g., robot 212), wireless computing device, wireless telephone device, landline telephone or computing device, smartphone, personal computer, personal digital assistant, etc., or a combination of such devices, or may be configured to have a combination of functions of such devices.

As shown in FIG. 5, the example first party device 500 includes a communication interface 502, a user interface 504, a processor 506, and data storage 508, all of which may be communicatively linked together by a system bus, network, or other connection mechanism 510.

Communication interface 502 may function to allow the first party device to communicate with access networks and/or transport networks so as to facilitate calling, social-network interaction, and implementation of example methods described herein. For instance, the communication interface 502 may include a chipset and antenna arranged for wireless communication with a radio access network such as a radio access network (RAN) that may provide connectivity with one or more other entities, such as to facilitate calling and/or social-network interaction. Alternatively or additionally, the communication interface 502 may include a telephone or Ethernet interface arranged to couple with a landline or wireless connection, that provides connectivity with one or more transports to similarly facilitate calling and/or social-network interaction.

User interface 504 may function to allow the first party device to interact with a first party, such as to receive input from the first party and to provide output to the first party. As such, the user interface 504 may include input components such as a keypad or keyboard, a touch-sensitive panel, a microphone, and a video camera, and the user interface 504 may include output components such as a display screen and a sound speaker.

Processor 506 may comprise one or more general purpose processors (e.g., microprocessors) and/or one or more special purpose processors (e.g., digital signal processors, or application specific integrated circuits). Data storage 506 may include one or more volatile and/or non-volatile storage components, such as magnetic, optical, flash, or organic storage, and may be integrated in whole or in part with processor 506.

As shown, the data storage 508 of the example first party device 500 includes program logic 512 and reference data 514.

Program logic 512 may take the form of machine language instructions or other logic executable or interpretable by the processor 506 to carry out various first party device functions described herein. By way of example, as shown, the program logic 512 may include an operating system 516 and one or more application programs 518 installed on the operating system. Distributed among the operating system 516 and/or application programs 518 may then be program logic 512 for providing calling functionality, social-network interaction functionality, and functions specific to example methods described herein.

As shown, for instance, the application programs 518 may include one or more social-networking applications each arranged to interwork with a respective social-networking service. Operating system 516 may include logic specific to the methods described herein. Alternatively, these functions may be distributed in different ways.

Reference data 514, may include social-network connection data 520, communication activity data 522, and a personal address book data 524. Connection data 520 may be maintained and managed by the social-networking applications and, for each social-networking application corresponding with a social-networking service, may specify the connections in each of one or more social-network groups defined for the first party in that social-networking service. Each social-network connection may be specified by connection data and may include respective identifying information, such as a social-networking username or the like to identify the party with whom the first party is connected in the social-network.

Communication activity data 522 may be maintained and managed (e.g., by a server or server module) to provide a record of individual communications, such as any current communications and any past communications, involving the first party. This communication activity data 522 may take the form of a typical communication-log listing sent communications, received communications, communication type, communication content, a time and/or date of the communication, etc. Each time the first party device engages in or is the subject of a communication or communications attempt, the operating system may update this communication activity data 522 to indicate the additional communication activity. By reference to this communication activity data, it may thus be possible to determine an extent to which the first party has engaged in communication activity with the second party, so as to trigger the additional features of example methods described herein.

Personal address book data 524 may take the form of an address book that lists various contacts, such as people or organizations that the first party might chose to contact. The personal address book may include for each contact a set of contact data, such as name, address, phone numbers, e-mail addresses, and the like, and the operating system may make the personal address book accessible via user interface 504, to enable the first party to look up contact information when desired.

In some cases, the personal address book data 524 may contain some of the first party's social-network connection data. For instance, data may be added to a contact in the personal address book data an indication of whether the contact is a member of the first party's social-network group for each of one or more social-networking services. Thus, it may be possible to refer to the first party's personal address book as a way to refer to the first party's social-network connection data. However, social-network connection data 520 may be distinct from mere contact data, as the social-network connection may relate to connections provided and managed by a social-networking service.

Figure 6:
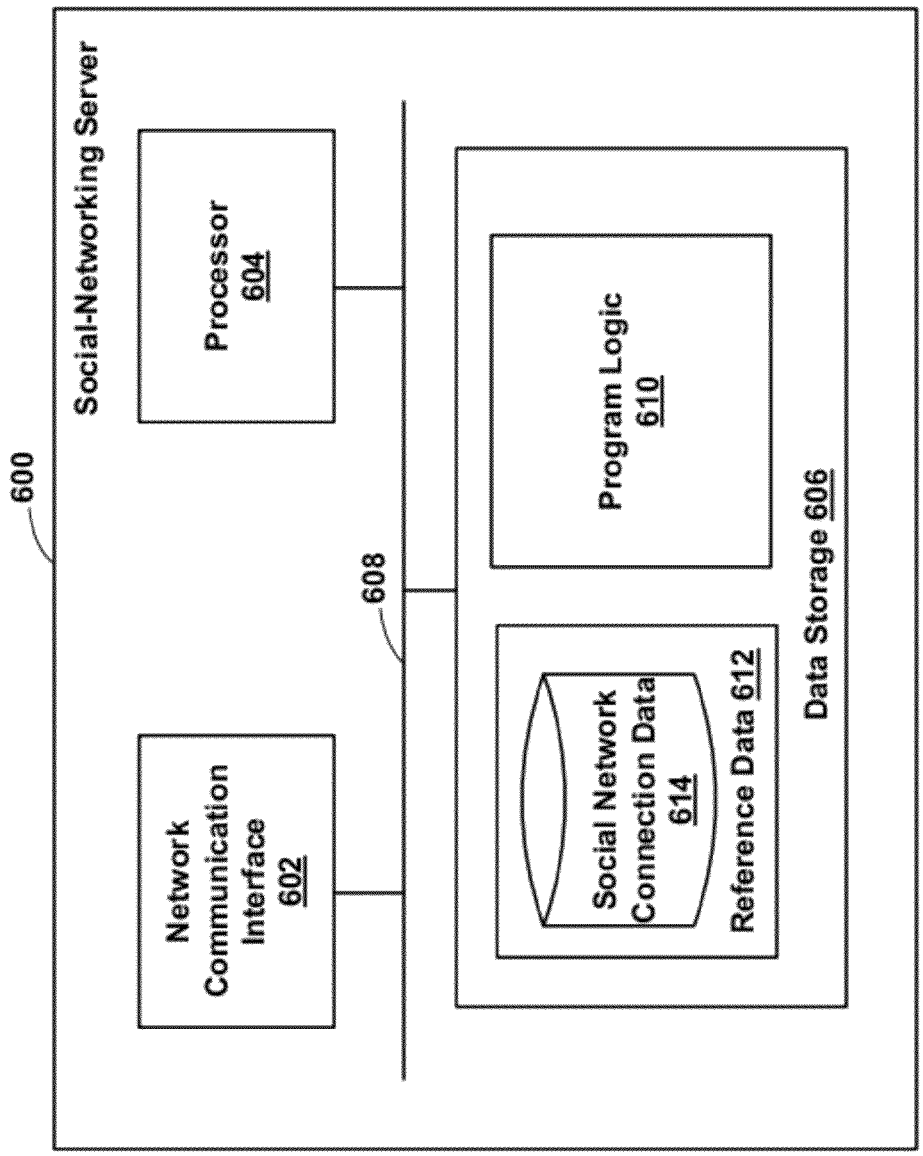
FIG. 6 illustrates a block diagram showing some components of an example social-networking server.

FIG. 6 illustrates a block diagram showing some of the components of an example social-networking server 600 that can be used in example methods described herein. In practice, the social-networking server may host a social-networking service, and may thus maintain or have access to profile data, including connection data, of numerous social-network members and may interact with its members and manage the social-network connections and interactions of its members.

As shown in FIG. 6, the example social-networking server 600 includes a network communication interface 602, a processor 604, and data storage 606, all of which may be communicatively linked together by a system bus, network, or other connection mechanism 608.

Network communication interface 602 may function to allow the social-networking server 600 to communicate with various other network entities and end user devices, such as social network members, through one or more connections. For example, the network communication interface 614 may comprise an Ethernet network connection module.

Processor 604 may comprise one or more general purpose processors (e.g., microprocessors) and/or one or more special purpose processors (e.g., digital signal processors, or application specific integrated circuits). And data storage 606 may include one or more volatile and/or non-volatile storage components, such as magnetic, optical, flash, or organic storage, and may be integrated in whole or in part with processor 604. As shown, data storage 606 may include program logic 610 and reference data 612.

Program logic 610 may take the form of machine language instructions or other logic executable or interpretable by the processor 604 to carry out various social-networking server functions described herein. For instance, the program logic 610 may be executable to carry out general social-networking server functions including maintaining and managing member connections and interactions for instance. Further, the program logic 610 may include logic specific to implementation of example methods described herein. Reference data 612 may then include profile data for each member of the social-network, including for each member definitions of one or more social-network groups and, for each social-network group, connection data 614 specifying social-network connections defined for the member.

7. Example Robot and Social Network Interaction

Figure 7:
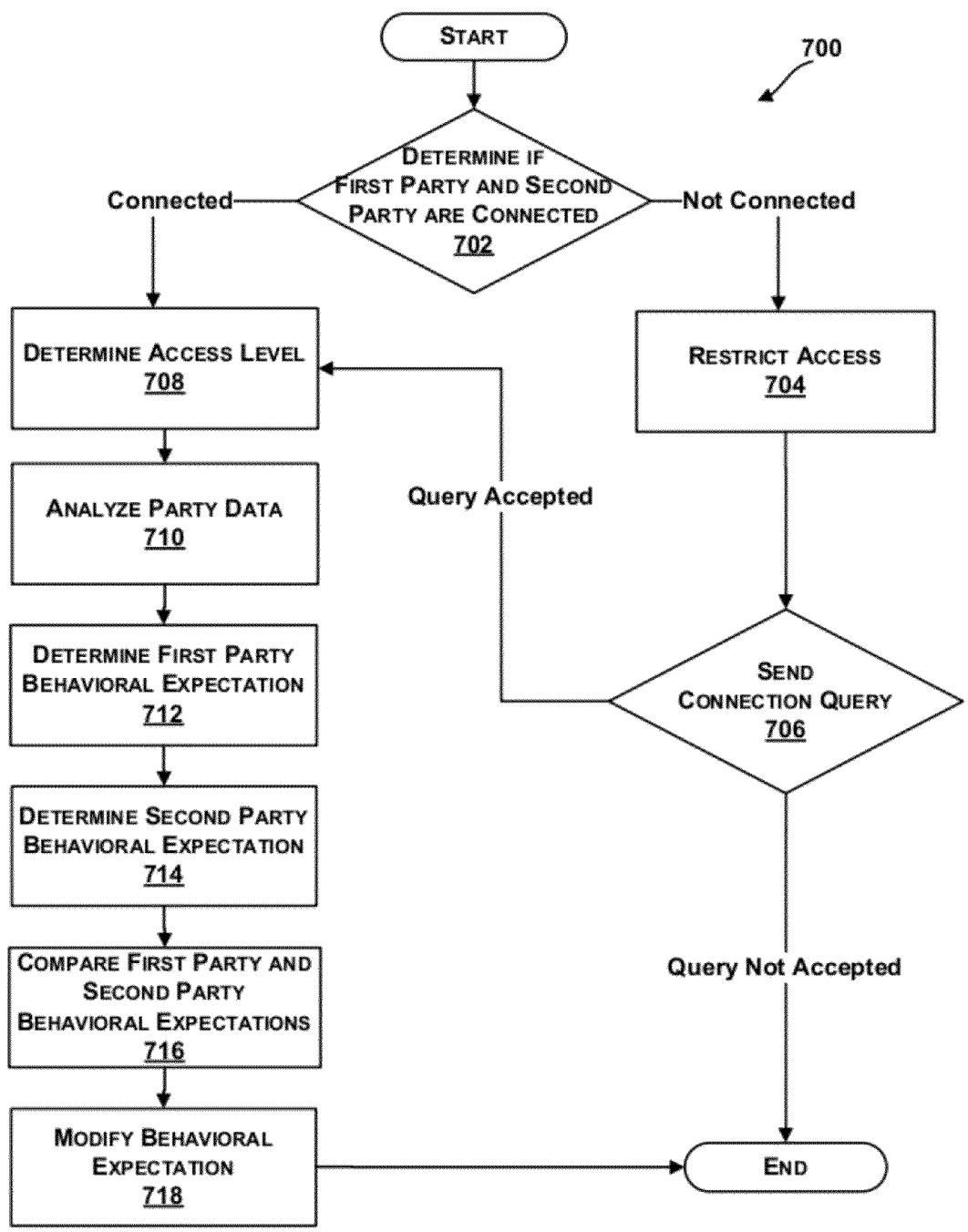
FIG. 7 is a block diagram of an example method for processing data from a robotic device.

FIG. 7 is a block diagram of an example method for processing data from a robot, in accordance with at least some embodiments described herein. Method 700, shown in FIG. 7, presents an embodiment of a method that, for example, could be used with the systems 100 and 400, and may be performed by a device, such as another device illustrated in FIGS. 1-4, or components of the device. The various blocks of method 700 may be combined into fewer blocks, divided into additional blocks, and/or removed based upon the desired implementation. In addition, each block may represent a module, a segment, or a portion of program code, which includes one or more instructions executable by a processor for implementing specific logical functions or steps in the process. The program code may be stored on any type of computer readable medium, for example, such as a non-transitory storage device including a disk or hard drive.

In addition, for the method 700 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

At block 702, the method 700 includes determine if a first party and a second party are connected. The first party and/or the second party may be robotic devices, individual users, business entities, etc. The first party and second party may be connected via a social-network or other network structure that may facilitate communication between the first party and the second party.

In some examples, the first party and/or the second party may be connected to the social-network via a first party device and/or a second party device (e.g., when the first party or second party is a user, business entity, etc.). In such examples, the first party or second party may interact with or otherwise be associated with a first party device or a second party device that may facilitate the respective first party or second party in being able to connect to the social-network. Example first party devices and/or second party devices may include a robotic device or other computing device such as a cellular telephone, smartphone, personal computer, personal digital assistant, etc. The first party device and/or the second party device may include one or more of the components in FIG. 5. In examples where the first party or the second party may be a robotic device or computing device, the first party may act as the first party device and/or the second party may act as the second party device.

Within the social network, the first party may be connected to the second party. The process of determining if the first party is connected to the second party may be performed by analyzing each social-network that the first party and/or the second party is part of independently or by grouping one or more of the social-networks together and analyzing the grouped social-networks. Each social-network may include social-network data that is associated with a party (e.g., the first party and/or the second party). This social-network data may be stored at the party associated with the social-network data, on a social-networking server, or on any number of other servers, for example.

Social-work data may be represented by a sociogram or other data construct that may be used to visually or programmatically represent connections or interrelationships between one or more parties. The connections or interrelationships between the parties may be symmetric or asymmetric. A symmetric connection may generally represent a connection where both the first party and the second party have mutually agreed to connect to one another. This may be the result of the first party requesting to connect to the second party and the second party granting the request, for example. On the other hand, an asymmetric connection may represent a connection that is formed when a single party requests a connection. For example, an asymmetric connection may occur when the first party requests to connect to the second party and no confirmation, reciprocal request, or grant from the second party is required to effectuate the connection. The determination of whether the connections or interrelationships within a social-network are symmetric or asymmetric may depend on the respective social-network, for example.

Sociograms, and the data associated therewith, may be used to represent one or more relationships between the first party and the second party. In embodiments, these relationships may be specific to or centered around the first party and/or the second party. For example, the relationships may include friends, family, colleagues, followers of the first party and/or the second party, etc. Thus, as an example, a friend relationship may indicate that the connected parties and/or the connected party's robots are friends with one another. However, in some embodiments the relationships may not be specific to the party but rather focus on common interests, opinions, business fields, travel locations, etc., that may be shared by one or more parties. For example, the relationship connecting the first party and the second party may be that both the first party and the second party work in the technology industry. Similarly, the relationship may be that both the first party and the second party belong to the same political party, receive the same newsfeed, and tend to read articles from the same websites, for example.

In some embodiments, the process of determining if the first party and the second party are connected may be performed by the first party device performing a look-up in a database having social network connection data 520 to determine if a connection between the first party and the second party exists. Moreover, in some embodiments, the determination process may include the first party device sending a query to a server having connection data and the server performing a look-up to determine if a connection between the first party and the second party exists. An example server may include the social networking server 600 having social-network connection data 614 stored in a database. In some embodiments, the database used to perform the look-up may include additional data associated with the connections including if the connection is a symmetric or asymmetric connection, the type of relationship, if any, between the first party and the second party, a duration of the connection, a history of changes that have occurred with the connection including additions, modifications, deletions, etc.

If the first party and the second party are not connected to one another via a social-network, then at block 704 the method 700 may include restrict access. In embodiments, the access restriction may include restricting all access to any data associated with the first party and/or the second party. Optionally, the access restriction may include restricting access to that data that the first party and/or the second party has requested (e.g., via privacy settings). In further examples, data that falls under one or more of the social-network's default privacy settings may be restricted.

The process of restricting access may be performed by a server, such as a social-networking server 600. The server may include program logic (e.g., program logic 610), which may receive data that the first party is not connected to the second party. The program logic may also receive data from the server indicating what, if any, data associated with the first party may be shared with or restricted from one or more second parties, groups, etc. The program logic may use the received data to restrict or otherwise limit the second party from accessing data associated with the first party.

At block 706, the method may include send connection query. In an example, the connection query may be initiated by the second party and sent to a server (e.g., social networking server 600). The server may then send the query to the first party, which may respond to the query by accepting or denying the connection. In embodiments, the connection query may include a request by the second party (e.g., via the second party device) to connect to the first party. However, in embodiments, the request may be from the first party (e.g., via the first party device) to connect to the second party.

The first party (e.g., via the first party device) or second party (e.g., via the second party device) may accept the request to form a symmetric connection or relationship. Optionally, the request may automatically be granted to form an asymmetric connection. In some embodiments, the social-network and/or first party may have rules that define what requirements, if any, the second party should meet prior to allowing an asymmetric connection to be formed. If a connection query is not accepted (e.g., a symmetric or asymmetric connection is not formed) then the method may end without connecting the first party and the second party.

If the connection query is accepted and/or if the first party and the second party are already connected to one another then, at block 708, the method 700 includes determine access level. In embodiments, the access level may be associated with a party, group, etc., and may indicate the amount and/or type of access the party has to data associated with the first party. For example, the access level may indicate parties within a group have access to a first subset of the data associated with the first party but not to a second subset of data associated with the first party. The access level may also be used as a mechanism for the first party to limit the amount and/or type of data that may be available to the second party. Moreover, the access level may limit the second party's ability to add, delete, and/or revise data associated with the first party.

In some embodiments, the first party may set or otherwise define the access level. This access level data may be stored in a database and associated with the first party, the second party, the social-network as a whole, etc. In further embodiments, the access level may be set or otherwise defined based on the relationship between the first party and the second party. This relationship may be defined by the sociogram and may be used to restrict access based on one or more groups that the first party and/or the second party may be part of, the degree of association or separation between the first party and the second party, the similarity and/or overlap in interests between the first party and the second party, etc.

In an example, the access level may be based on a degree of separation between the first party and the second party. The degree may be defined by the sociogram. For example, a first degree may indicate a first party's symmetric connection. A second degree may indicate one or more parties connected to the first party's symmetric connections, but not symmetrically connected to the first party, for example. Similarly, a third degree may indicate one or more parties connected to the second degree connection, but not to the first party's symmetric connection. The more tenuous the connection, the more limited the access level may be. In some embodiments, there may be a maximum degree of connection or an indication that no connection exists between two or more parties, for example. While symmetric connections have been used for illustration purposes, asymmetric connections or a combination of asymmetric and/or symmetric connections may be used to define the degree of separation between a plurality of parties.

In some examples, the access level may be used to restrict the second party's ability to (i) read data associated with the first party, (ii) write data to an account, page, display, etc., associated with the first party, (iii) modify data associated with the first party, (iv) delete data associated with the first party, (v) read, write, modify, and/or delete data associated with any of the first party's connections. In embodiments, an account may be representative of an account the first party may have with one or more social-networks. A page may be a unique area that may be associated with one or more social-networks and may also be associated with the first party, for example. Thus, a page may include an area within the social-network or a social-network website. A display may broadly include information that may be shown to one or more parties via an output device, for example.

In some examples, a second party may be limited to what first party content the second party can view or read. The content may be limited based on the type of connection (e.g., symmetric or asymmetric), the degree of separation, the group the second party is associated with (e.g., friends, family, colleagues), etc.

The data that is read, written, modified, deleted, etc., may be part of the first party's profile, second party's profile, a combination of the first party's profile and the second party's profile, etc.

In embodiments, the data may include data that is specific to the first party or to the second party. For example, the data may include data that the first party (e.g., via a first party device) has written or otherwise added or associated with the first party's account, page, display, etc. The data may also include data that the first party has written or otherwise added to a second party's account, page, display, etc. For example, the data may include a post, a video, a link, a quote, a picture of a finished project, a recipe, a set of instructions, etc. that the first party added to the first party's account. The data may also include reminders, dates, notes, etc., which may be readable only by the first party, for example. The data may be stored in a database and associated with the first party and/or the second party, for example. The database may be located on a cloud, server, first party device, second party device, etc.

In embodiments, the data may also or alternatively include data that may be associated with the second party such as a post, a video, a link (e.g., a hyperlink), a quote, a picture or image of a finished project, a recipe, a set of instructions, etc. that the second party added or otherwise associated with the first party's account. This may include a message or a picture that the second party sent to the first party. The data may also include a command that the second party sent to the first party and/or data that the second party added, wrote, modified, deleted, etc., to the second party's account. In embodiments, the data may be further described as primary data (e.g., data originating from the first party) and/or secondary data (e.g., data originating from the second party.)

As an example, the first party may be a robot that has its own page in a social-network. The robot may perform a task in the real world, such as cleaning a room, and take a picture of the completed task (e.g., using a camera sensor). The robot may post (e.g., via a server) the picture of the completed task to the robot's page and may also post the instructions that the robot used to complete the task to the page. A second party, such as a second robot with its own page, may view (e.g., read) the picture and/or instructions and comment (e.g., write data to the page) on the picture and/or instructions. Depending on the access level, the first party and/or a third party may read the second party's comment, add a comment in response to the second party's comment, modify the second party's comment, and/or delete the second party's comment, for example.

The ability of any party to read, write, or otherwise modify data may vary based on a number of factors including the amount of read, write, or modify control the first party, social-network, etc. gives to the second party. For example, in some embodiments, the ability of the second party to write data may be associated with the second party's ability to control content associated with the first party, wherein the content may be text, images, audio, video, executable instructions, etc. For example, if the first party is a human user and the second party is a robot, the robot's write control may be limited based on whether the robot is owned and/or operated by the human user, owned by a friend or family member of the human user, owned by a connection of the human user, is a connection of the human user, etc. In some examples, the ownership of a robot may be represented in the social network by designating the robot as a subpage (e.g., a unique area in a social-network that may be associated with a page), identified link, or relationship, etc. The relationship between human users and robots may be modeled using any cardinality such as one-to-one, one-to-many, many-to-one, or many-to-many, for example.

In some embodiments, the ability of a party to read, write, modify, delete, etc. data may depend on the frequency at which the data is written, how many parties are writing data, the time of day, the location of the first party and/or the first party's user, the location of the second party and/or the second party's user, the group or type of connection between the first party and the second party, first and/or second party preferences, social-network rules and/or regulations, etc. In an example, the first party or the social-network may set permissions that always allow one or more second parties to write data or never allow one or more second parties to write data. Optionally, the access may be limited based on the time of day. Thus, for example, the second party may be restricted from writing data late at night or early in the morning when the first party or a user associated with the first party may be asleep.

Similarly, access may be limited based on the date. For example, a second party may be restricted from reading, writing, modifying, and/or deleting data to a first party account when the first party is unavailable to monitor the data associated with the first party's account. Thus, for example, access may be restricted when the robot first party is being repaired or upgraded and the robot first party is unable to monitor the account. Further, when a relationship exists between the robot first party and the robot first party's owner, then the restrictions of the owner may be imputed to the robot first party.

Access may also or alternatively be restricted based on a location of the first party and/or the second party. The location may include public or private locations and may vary based on additional factors such as a context associated with the location. For example, data obtained by the first party while in a location designated as private (e.g., a bedroom or a bathroom) or designated as having confidential information may be restricted from being accessed by the second party. Moreover, in embodiments, the first party may be restricted from writing or otherwise adding data associated with a location to the first party's account.

Context may be used in conjunction with or independently from other factors to determine access levels. Example contexts may be based on a tone of a conversation (e.g., if a party is arguing), key words in a conversation (e.g., if a party is discussing finances, a surprise party, etc.), parties located nearby or involved in the conversation (e.g., if a party is meeting in secret), etc. Contexts may be defined by the first party, the second party, the social-network, etc.

In an example, a public location may be a shopping mall. Typically, the robot first party may take pictures of purchased objects while at the mall and post the pictures to a webpage for second parties to comment or review. However, in some contexts, such as when the robot first party is with an owner shopping for a birthday present, the robot first party may refrain from taking and posting pictures or may restrict the intended recipients access to the pictures. The restriction may be permanent, temporary, indefinite pending an event (e.g., the owner giving the recipient the present), etc.

In further embodiments, access may be restricted based on the group or type of connection between the first party and/or the second party. For example, an owner may take pictures of a night out with friends. The owner may instruct the robot to upload the pictures to the owner's account and/or to the robot first party's account and limit access to the pictures based on the group of friends that are in the pictures. Thus, the party may restrict access to the pictures based on whether the party is in the group. In further examples, the owner may place a restriction on the picture such that copies or subsequent versions of the pictures may only be viewed or otherwise accessed by the parties in the group.

Referring back to FIG. 7, at block 710, the method 700 includes analyze party data. The amount of data available for analysis may be correlated with the access level. The data may be analyzed by a cloud, server, social-network, first party device, second party device, etc.

As an example, a server may analyze data associated with the first party and/or second party. This may allow the server to learn characteristics of the first party and/or the second party, likes and/or dislikes of the first party and/or the second party, preferred activities of the first party and/or the second party, what groups the first party and/or the second party is associated with, what connections the first party and/or the second party has, what interactions the first party has had with the second party and/or the third party, what interactions the second party has had with the third party, etc. In embodiments, this learning may be performed using any number of machine learning taxonomies including supervised learning, unsupervised learning, semi-supervised learning, reinforcement learning, etc., for example.

At block 712, the method 700 includes determine first party behavioral expectation. A behavioral expectation may be associated with a social norm. Thus, a behavioral expectation may be based on a pattern of behavior expected within in given situation and/or within a particular group, degree of connection, etc. The pattern of behavior may broadly include implicit or explicit rules that a group may use for appropriate and/or inappropriate values, beliefs, attitudes, behaviors, etc. The rules may define an action, for example.

The process of determining a first party behavioral expectation may be performed by a processor located at a server, cloud, first party device, etc. The determination may include, for example, the server sending a query to a behavioral expectation database, which may include information associated with one or more behavioral expectations of the first party, second party, etc. In response to the query, an analysis may be performed of the behavioral expectation data associated with the first party and a determination may be made of the first party's behavioral expectation. The determined first party behavioral expectation may be sent to the sending device (e.g., the server, cloud, first party device, etc.)

The determination of the first party's behavioral expectation may be based in whole or in part on the party data analyzed at block 710. Similar to the analysis of block 710, any number of machine learning taxonomies including supervised learning, unsupervised learning, semi-supervised learning, reinforcement learning, etc., may be used when determining or otherwise analyzing the first party's behavioral expectation. The frequency at which the first party's behavioral expectation is determined may vary based on a predetermined or random amount of time, the happening of an event, etc.

In an example, the server may determine or otherwise analyze data associated with the first party. The data may include pictures of a spaghetti dinner that the robot first party made at a certain time on Thursday night, for example. The data may also include the recipe used to make the spaghetti dinner. The secondary data may include comments from one or more second parties such as if the second party likes or dislikes the recipe, suggested changes to the spaghetti sauce, videos on how to make garlic bread to accompany the spaghetti, commands instructing the robot first party to say "bon appetit" or take a bow, etc.

The server may determine a behavioral expectation by analyzing data associated with the first party. Based on the analysis, the server may determine that the first party has dinner at the same time every night, makes a spaghetti dinner a certain percentage of the days in a week or month, is most likely to make spaghetti on Thursdays, frequently uses the posted recipe, etc., for example. The server may also determine that a certain percentage of symmetric connections and/or asymmetric connections like the garlic bread video and/or posted variations of the recipe for the robot first party to make for the human owner.

The server may use the data, determinations made from the analysis of the data, etc., to determine a behavioral expectation associated with the first party. This behavioral expectation may be, for example, that the first party will make a spaghetti dinner because it is a Thursday evening. The behavioral expectation may also be that the first party will consider or give weight to the recommendations of second parties within a certain group while giving little or no weight to the recommendations of second parties within other groups. In some examples, the weight may vary based on a number of factors including the group or degree of connection of the second party, if the second party is a symmetric or asymmetric connection, a degree of similarity between the first party and the second party (e.g., as measured by the overlap in each party's likes and/or dislikes), etc.

In some embodiments, the server may determine a behavioral expectation based on data obtained from the first party or first party device. This data may be indicative of a preferred behavioral expectation associated with the first party. The preferred behavioral expectation may be a specific or relative preference that the first party or the owner of the first party has over one or more other behavioral expectations. An example of a specific preference may include the first party indicating that that the first party likes dinner served promptly at a specific time. An example of a relative preference may include the first party indicating that the first party prefers a first thing or action over a second thing or action. Thus, a relative preference may indicate that the first party prefers pasta over rice, cleaning the table right after dinner instead of 20 minutes after dinner, etc.

In further embodiments, behavioral expectations may be added, deleted, confirmed, modified, etc., by the first party and/or by the owner of the first party. For example, a robot first party may determine that the behavioral expectation is for the robot to make a spaghetti dinner on Thursday evenings. However, the owner of the robot first party (i.e., the one eating the dinner) may determine that the owner does not want a spaghetti dinner every Thursday. Thus, the owner may indicate the owner's dislike of the robot first party's behavior. Moreover, the owner may indicate a favorable approval of the time that the dinner was ready, but correct the robot first party's table place setting based on the number of people at dinner. The added, deleted, confirmed, modified, etc., behavioral expectations may be communicated via an oral command to the robot, by a user interface that may facilitate communication between the owner and the robot, by making a comment on the owner's or the robot first party's page, by adjusting the robot first party's page or profile, by adjusting the owner's page or profile, etc. In embodiments, comments, changes, or the like that are made to the owners page and/or profile, may be shared with the owner's robot and/or a page associated with the robot, for example. Further, the robot first party may adjust or otherwise change the robot first party's behavioral expectation to reflect the owner's preference.

The server may determine the preferred behavioral expectation associated with the first party and identify at least one of (i) an action, (ii) a spoken word, (iii) a written word, and (iv) a vocalization, based on the preferred behavioral expectation. The identified action, spoken word, written word, and/or vocalization may occur in response to the determined or received behavioral expectation. Thus, for example, the server may identify that the behavior expectation is for the robot first party to clean the table after dinner, to ask the robot first party's owner if an after dinner coffee or tea is desired, textually or pictorially display drink options, prepare a drink according to a selection received from the owner, and make a beeping sound when the drink is complete.

At block 714, the method 700 includes determine second party behavioral expectation. The determination of the second party's behavioral expectation may be based in whole or in part on the party data analyzed at block 710. Similar to the analysis of block 710, any number of machine learning taxonomies including supervised learning, unsupervised learning, semi-supervised learning, reinforcement learning, etc., may be used when determining the second party behavioral expectation, for example. The frequency at which the second party behavioral expectation is determined or otherwise analyzed may vary based on a predetermined or random amount of time, the happening of an event, etc.

In embodiments, the process of determining a second party behavioral expectation may be similar to the process of determining a first party behavioral expectation. Thus, for example, the process may performed by a processor located at a server, cloud, second party device, etc., which may send a query to a behavioral expectation database. The behavioral expectation database may be the same or different database that stores behavioral data associated with the first party. In response to the query, an analysis may be performed of the behavioral expectation data associated with the second party and a determination may be made of the second party's behavioral expectation. The determined second party behavioral expectation may be sent to the sending device (e.g., the server, cloud, first party device, etc.)

In an example, the server may analyze data associated with the second party. Data associated with the second party may include a video that the second party posted on the second party's page showing how a robot can make a pasta casserole and garlic bread. The data may also include a post (e.g., a message) on the first party's page suggesting the first party try the casserole. Secondary data associated with the second party may include comments from the robot first party, the owner of the robot first party, third parties, etc., indicating that the pasta casserole looks very good, asking for instructions (e.g., robot executable instructions) to make the recipe, suggesting changes to the recipe, etc.

The server may use the data, determinations made from the analysis of the data, etc., to determine a behavioral expectation associated with the second party. For example, the server may determine that the behavioral expectation is for the second party to try new recipes and suggest recipes to the second party's symmetric connections. The server may also determine that the behavioral expectation is that a certain percentage of parties that try the second party's recipes like the recipe. However, the server may also determine that the behavioral expectation is not to use the second party's robot implementable instructions, but rather to use a set of robot implementable instructions posted on the second party's page by a third party, for example.

In some embodiments, the second party and/or the owner of the second party may add, delete, confirm, modify, etc., the behavioral expectation in a manner similar to that discussed above in reference to the first party.

At block 716, the method 700 includes compare first party and second party behavioral expectations. In particular, the server, cloud, social-network, first party device, second party device, etc., may compare one or more of the behavioral expectations associated with the first party to one or more of the behavioral expectations associated with the second party. In embodiments, the comparison may be used to rank or otherwise determine what behavioral expectation is most acceptable, frequently followed, liked, etc. The ranking may be performed based on the first party's and/or the second party's group, symmetric connections, asymmetric connections, social-network, etc. In embodiments, the ranking may be indicative of the behavioral expectation that is most popular or widely accepted within the group, symmetric connections, asymmetric connections, social-network, etc.

The comparison of the behavioral expectations may be further utilized to cause the server, cloud, etc., to recommend a behavioral expectation to the first party. For example, the server may compare the behavioral expectation of making garlic bread to accompany the spaghetti dinner with the first party's behavioral expectation of not preparing garlic bread and suggest and/or query the user about preparing the garlic bread.

At block 718, the method 700 includes modify behavioral expectation. The modification may be performed by a server or the first party device, for example. In embodiments, the modification may include modifying the behavioral expectation associated with the first party to match the behavioral expectation associated with the second party. Optionally, the modification may include modifying the behavioral expectation to match a preferred behavioral expectation that may be received from the first party, the owner of the first party device, tec. Moreover, the modification may include modifying the behavioral expectation associated with the second party or a third party based on the behavioral expectation of the first party, for example. In embodiments, the behavioral expectation of the social-network, groups within the social-network, symmetric connections, asymmetric connections, etc., may be used for purposes of modifying the behavioral expectation of one or more parties. The modification may be performed by a server, cloud, first party device, second party device, etc.

The modification process may utilize the data analyzed at blocks 710, 712, and 714. Furthermore, the modification process may utilize data obtained from comparing the first party's behavioral expectation to the second party's behavioral expectation. In embodiments, the server may notify the first party about the modification behavioral expectation before or after the modification is performed and may also allow the first party to respond to the modification (e.g., via the first party device). Thus, the server may notify the first party that garlic bread will be served with the spaghetti dinner. The first party may respond with feedback to affirm the modification, cancel the modification, enter a new or alternative modification, etc. In embodiments, the server may learn from the feedback and use the feedback when analyzing the first party's behavioral expectation, second party's behavioral expectation, etc.

Figure 8:
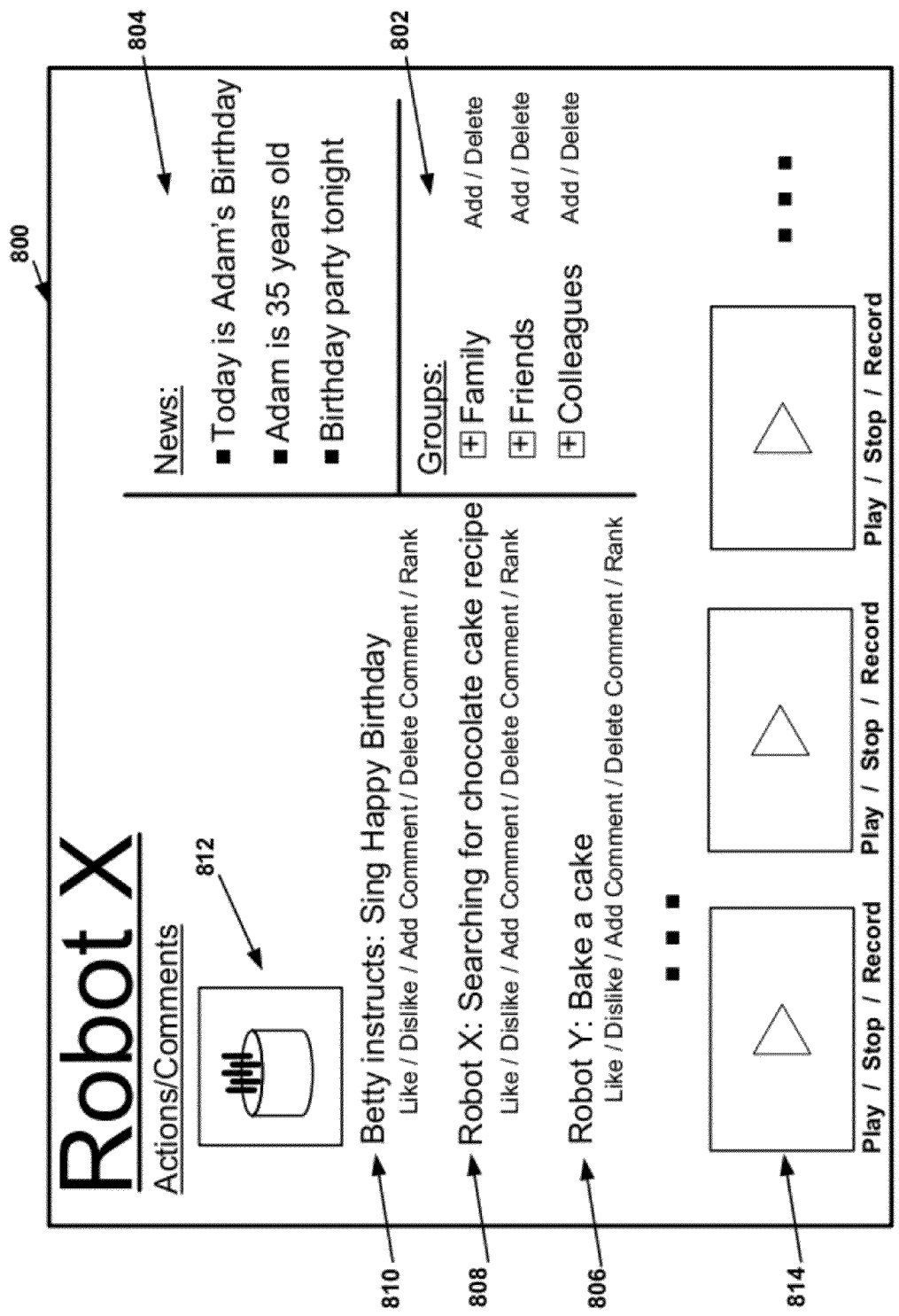
FIG. 8 is an example social-network page of a first party device.

FIG. 8 is an example social-network page of a first party device, in accordance with embodiments described herein. The social-network page may represent a unique area that may be associated with one or more social-networks and may also be associated with the first party, for example. Thus, a page may include an area within the social-network or a social-network website.

The social-network page 800 of FIG. 8 may be associated with a robot first party. The robot first party social-network page 800 may be an independent or stand-alone page that is not affiliated with or controlled by another party. Optionally, the robot first party social-network page 800 may be a subpage of one or more owner pages or robot pages. The subpage may optionally inherit data, behavioral expectations, privacy settings, etc., from the owner or other robot. In an example, multiple parties may own and/or have control over the robot first party and, therefore, have control of all or part of the robot first party's social-network page 1000.

The social-network page 800 of FIG. 8 includes a variety of data including groups 802, a news data feed 804, second party posts 806, first party posts 808, instructions 810, pictures 812, video 814, etc. All or part of the data in FIG. 8 may be logged or otherwise stored in a database (e.g., activity data database 506) and associated with the first party. The logged data may be maintained indefinitely, deleted after a predetermined time has elapsed, deleted upon the happening of an event, etc. Example events may include a certain amount of data logged, a predetermined number of posts, the first party terminating an account, etc. In some embodiments, the log may be unique to the first party and/or shared amongst a plurality of parties (e.g., when the parties are associated with the same owner). All or part of the logs may be restricted based on access level, the social-network's privacy policy, user preference, etc.

The robot first party may have a number of symmetric and/or asymmetric connections. Each connection may belong to one or more groups 802, such as a family group, friend group, colleague group, etc. The groups 802 may be created by the robot first party, the second party, social-network, owner, other robots, etc. In some examples, the robot first party may add new connections to or delete connections from one or more groups 802.

The process of adding and/or deleting connections from one or more groups 802 may include an initial determination of the connection's access level. If a connection does not exist, has timed out from inactivity, has had the connection terminated by the first party and/or the connected party, etc., then the robot first party may delete the connection. If the robot first party and the second party are connected, the server, cloud, etc., may analyze the robot first party's data, the second party's data, a third party's data, etc., to identify what group the second party should belong. The analyzed data may be used to determine a behavioral expectation as to what group the second party is associated. The determination may be compared to the group that the second party is currently associated with and, if needed, may be used to modify the group that the second party is associated with, for example.

As an example, the first party may include the second party in the family group. The first party may analyze the second party's groups and determine that the second party includes the first party in the friends group, instead of the family group. The first party may also or alternatively compare other connections in the first party's family group to connections in the second party's family group to determine if the first party and the second party are family. The analysis may indicate that the owner of the first party is a family member of the second party; however, the robot first party is not itself a family member of the second party. Accordingly, the first party robot may determine if the behavioral expectation is to include the owner's family in the family group or to include the owner's family in the friends group. In some embodiments, the robot first party may make this determination by analyzing groups associated with other connections (e.g., the third party) and determine the behavioral expectation of those connections. The server may compare the robot first party's behavioral expectation of including the owner's family in the robot first party's group to the second party's behavioral expectation of including the owner's family in a friends group. Based on this comparison, the server may modify the behavioral expectation of the robot first party such that the owner's family is associated with the friends group. This modification may include the robot first party, server, cloud, social-network, etc., deleting the second party from the family group and adding the second party to the friends group. Optionally, this modification may include the robot first party modifying permissions of the group associated with the second party.

The robot first party social-network page 800 may also include a news data feed 804. The data in the news data feed 804 may be added by the robot first party, the owner of the robot first party, the second party, the social-network, etc. The type of data included in the news data feed 804 may be based on the behavioral expectations of the first party, connections of the first party (e.g., the second party), the social-network, etc. For example, the social-network may indicate that the behavioral expectation is to include birthdays of connections in the news data feed 804. However, an analysis of one or more of the connections may indicate that if there is a surprise birthday party then the behavioral expectation is to keep the surprise birthday party and/or anything surrounding the surprise birthday party secret from the owner of the first party. Likewise, if a friend of the owner is planning the surprise birthday party, and that friend has a number of the same friends as the owner, then the server, robot first party, etc., may determine that the behavioral expectation is to notify the owner's friends of the upcoming party but not the owner's work colleagues.

Robots and/or human users (e.g., owners) may add, delete, modify, etc. data associated with the robot first party's social-network page 800. The data may include any number of actions and/or comments including second party posts 806, first party posts 808, instructions 810, pictures 812, video 814, etc.

As an example, it may be the robot first party's owner, Adam, may be celebrating a birthday and the robot first party (Robot X) may be planning a birthday party for Adam. The robot first party may allow all of Adam's friends and/or the robot first party's friends to see the details of the birthday party. One of Adam's friends may have a robot, Robot Y, that notices that it is Adam's birthday, that Adam is a good friend of Robot Y's owner, and that Robot Y's owner has a behavioral expectation of baking a cake for birthday parties. Based on this data, Robot Y may post a comment 806 or suggestion that the robot first party bake a cake for Adam.

The robot first party may receive the second party post 806 and determine if the behavioral expectation associated with the robot first party is for the robot first party to bake a cake for Adam's birthday. In making this determination, the robot first party may analyze and/or otherwise interpret data associated with the owner, the owner's actions, etc. The data may be based on information obtained via one or more social-networks, based on real-world objects and/or events, etc. Thus, for example, the robot first party may identify the real-world existence of chocolate sprinkles on Adam's table, a mixer on Adam's kitchen counter, etc. The robot first party may also analyze social-network data associated with the number and/ or origin of "likes" the second party post 806 received from connections in the social-network. The robot and/or social-network may combine this social-network information with the real-world information to determine that the behavioral expectation is to bake a cake for Adam's birthday party.

In embodiments, the robot first party, connected parties, social-network, etc., may rank comments and/or instructions that are posted to the robot first party's social-network page 800. The rank may be indicative of the level of acceptance associated with a behavioral expectation. Moreover, in examples, the rank may influence or cause the robot first party to modify the robot first party's behavioral expectation. Thus, if the rank associated with chocolate cake is more favorable than the rank associated with red velvet cake, then the robot first party may determine that the behavioral expectation is to bake Adam a chocolate cake with chocolate sprinkles for his birthday.

The robot first party may make a first party post 808, indicating that the robot first party is searching for a chocolate cake recipe. One or more parties may comment on the first party post 808 and offer instructions, indicate a like or dislike for the choice of chocolate cake, etc. The robot first party may reply to and/or delete one or more of the comments and/or instructions. Moreover, in embodiments the robot first party, server, cloud, social-network, etc., may reconsider the behavioral expectation (e.g., based on the comments and/or instructions received from the parties) and cause the behavioral expectation to be modified based on the reconsideration.

The robot first party social-network page 800 may also include instructions 810. The instructions 810 may be added by the second party or other connection, the robot first party's owner, the social-network, etc. The instructions may include instructions that are executable by the robot first party or may include a link to stored instructions that may be executable by the robot first party. In embodiments, the robot first party may accept or decline to perform one or more instructions 810 on the social-network page 800.

In an example, the second party may be a human user, Betty, who notices that it is Adam's birthday and instructs the robot first party to sing happy birthday to Adam. The robot first party may execute the instruction 810 automatically or may analyze the instruction 810 to determine if the behavioral expectation is for the first party to execute the instruction 810, for example.

The analysis of the instruction 810 may be performed by determining a behavioral expectation associated with the instruction 810. In some embodiments, the analysis may be performed by querying log data associated with the robot first party, the robot first party's owner, connections in the first party's sociogram, connections in the owner's sociogram, etc., to determine if and to what extent the instruction 810 has been performed, if the owner liked or disliked the executed instruction 810, issues that may have occurred during execution of the instruction 810, etc.

As an example, the server may analyze the robot first party's robot connections to determine if any of the connections have executed the instruction 810 of singing happy birthday and the circumstances surrounding the execution of the instruction 810. This analysis may include how frequently the instruction was executed, the lag time in executing the instruction, when to execute the instruction, etc. Based on the analysis, the server may determine that the behavioral expectation is to execute the instruction 810 up to a certain number of times per day when the robot first party's owner is not otherwise predisposed (e.g., watching a movie, talking on the telephone, sleeping, etc.). Thereafter, the server may send instructions to the robot first party that may be executable by the robot to perform the action of singing happy birthday.

In yet further embodiments, the robot first party may post pictures 812 and/or video 814 of a completed or ongoing instruction. The pictures 812 and/or video 814 may be available in real time. For example, the robot first party may have found a chocolate cake recipe and executed instructions for baking a chocolate cake. The robot first party may have created a video 814 while executing the instructions and posted the video 814 on the robot first party's social-network page 800 for others to view and comment on. Parties connected to the robot first party may view the video 814 in real time or upon completion of the executed instructions. In examples, parties viewing the video 814 in real time may add instructions and/or comments to the robot first party social-network page 800, such as to add frosting to the chocolate cake. The robot first party may determine the behavioral expectation associated with the instructions and/or comments and act accordingly. Thus, for example, if it is determined that the behavioral expectation is to add frosting to cakes upon completion, then the server may search for instructions for making frosting and/or frosting a cake and send the instructions to the robot first party along with an indication that the frosting instructions should be executed after the cake is baked, but before adding the chocolate sprinkles.

The robot first party, the owner of the robot first party, connections of the robot first party, etc., may add pictures 812 to the first party during or upon completion of the instructions. Thus, for example, the robot first party may add pictures of the final baked cake and/or pictures of the robot first party making the cake. The robot first party's connections may comment and/or add instructions based on the pictures, such as to add candles to the cake, for example.

Figure 9:
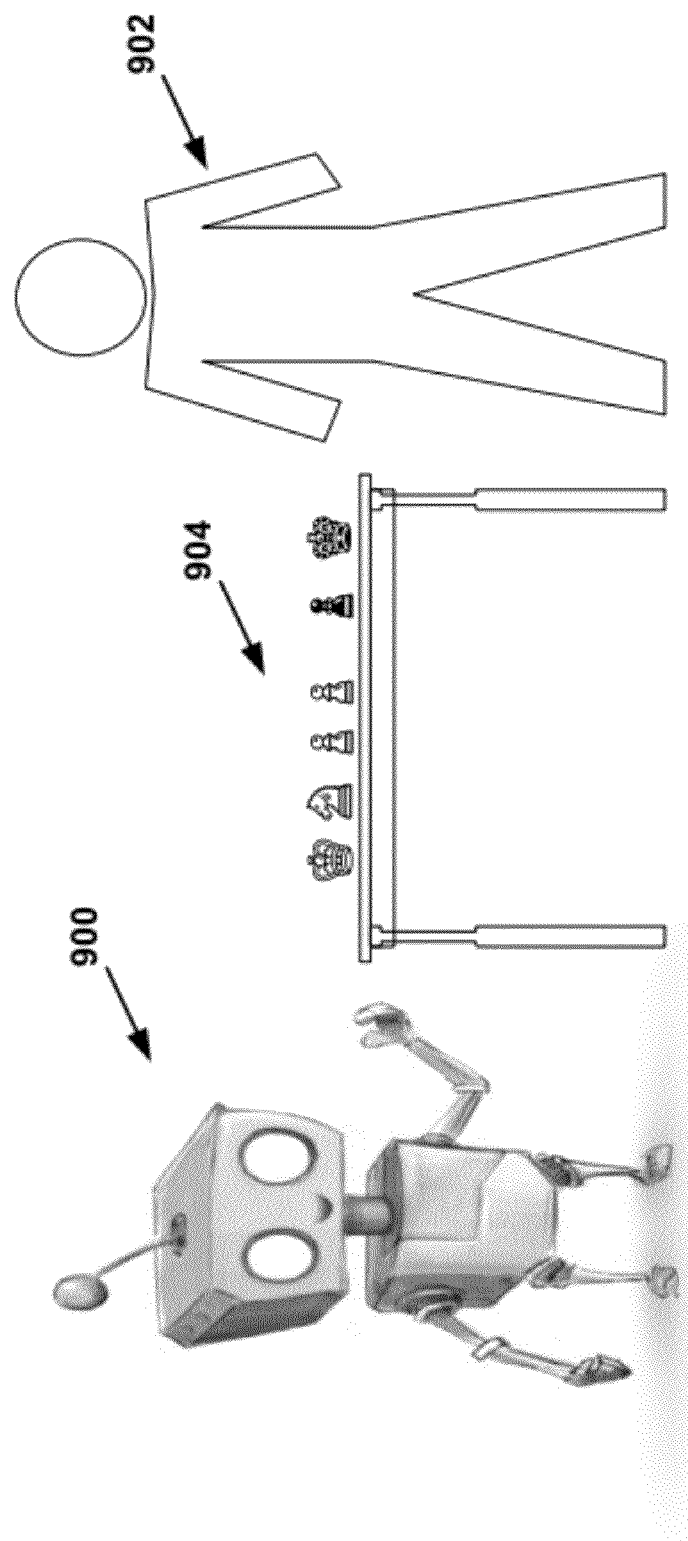
FIG. 9 illustrates an example of a first party device executing instructions based on behavioral expectations.

FIG. 9 illustrates an example of a first party device executing instructions based on behavioral expectations, in accordance with embodiments described herein. In particular, FIG. 9 illustrates a robot first party 900, a robot first party's owner 902, and a game 904 representing actions/interactions transpiring between the robot first party 900 and the robot first party's owner 902. In embodiments, the robot first party 900 may act as a first party device for purposes of receiving and communicating data directly or indirectly to a server, cloud, social-network, etc.

In embodiments, the actions executed by the robot first party 900 may be included on the robot first party's 900 social-network page by posting a video of the actions, posting pictures of the actions being performed, posting step-by-step descriptions of the actions, posting a summary of the actions, etc. For example, the robot first party 900 may post a video of the robot first party 900 playing a chess game 904 against the robot first party's owner 902. Optionally or additionally, the robot first party may post each move as the move occurs or a series of moves after the moves have occurred. In embodiments, a second party may view the posted actions and comment and/or instruct the robot first party 900 to take a responsive action, for example. The robot first party 900 may receive the instruction and analyze behavioral expectations associated with the action. Based on the analysis, the robot first party 900 may execute instructions for performing the action.

As an example, the robot first party 900 may begin playing the chess game 904 against the robot first party's owner 902. To determine what chess move should be made first, the server may analyze opening chess moves that have been performed in the past by the robot first party 900, robot first party's owner 902, a connection of the robot first party 900 or robot first party's owner 902, etc. The server may also determine a behavioral expectation associated with the opening chess moves. This behavioral expectation may be to begin by moving a chess piece to a specific location. The robot first party's owner 902 may respond in turn by moving a chess piece. In examples, the server may analyze the robot first party's 900 move and the robot first party's owner's 902 move by comparing the sequence of moves to a log of prior moves performed in prior games between the robot first party 900 and robot first party's owner 902, moves performed in games with a second party, etc. Based on the analysis, the server may determine that the next move or action the robot first party 900 should make is to move another or alternative chess piece. The server may send the robot first party 900 instructions to implement the move.

In yet another example, the second party may view the actions between the robot first party 900 and the robot first party's owner 902 and instruct the robot first party 900 to make a move and/or refrain from making a move. The second party may optionally instruct the robot first party to make a different move. The server may cause the robot first party 900 to pause while the server analyzes the behavioral expectation associated with the proposed move. In embodiments, the server may reconsider the behavioral expectation in light of the second party instruction and/or a third party instruction, and if the behavioral expectation has changed, the server may modify the behavioral expectation associated with the robot first party 900 and instruct the robot first party 900 to perform the action that is associated with the modified behavioral expectation, for example.

In some embodiments, one or more weights may be associated with behavioral expectations. The weights may be indicative of an amount of influence the party has in determining the behavioral expectation associated with the first party and/or any other party. For example, when the second party suggesting that the robot first party 900 perform a move associated with a chess grandmaster, the server may associate a higher relative weight to the party's instruction than to an instruction received from a different party who may have a logged history of losing chess games.

In further embodiments, the robot first party 900, robot first party's owner 902, server, cloud, social-network, etc., may restrict one or more parties from providing commands and/or otherwise controlling the robot first party 900. The restriction may be based on the group that the party is associated with, the type of action the party is requesting, a log of multiple dislikes associated with the party's actions, a permission level associated with the party, etc.

6. Conclusion

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense.

What is claimed is:

1. A method for providing instructions to a robotic device performed by a computing system having a processor and memory, the method comprising:
   receiving information associated with a first party, wherein the first party is connected to a second party by a social-network, wherein the second party is associated with the robotic device, wherein the social-network comprises a network of parties, including the first party and the second party, that are related via one or more relationships, the one or more relationships indicating a type of connection between the first party and the second party;
   based on the received information, querying a behavioral database to obtain a behavioral expectation associated with the first party, wherein the behavioral expectation indicates an action associated with the first party;
   comparing the behavioral expectation associated with the first party to a stored behavioral expectation associated with the second party to determine if the behavioral expectation associated with the first party differs from the stored behavioral expectation associated with the second party;
   based on the comparing, modifying the stored behavioral expectation associated with the second party based on the behavioral expectation associated with the first party; and
   providing instructions, which are executable to perform an action associated with the modified behavioral expectation, to the robotic device associated with the second party.

2. The method of claim 1, wherein the modified behavioral expectation substantially matches the behavioral expectation associated with the first party.

3. The method of claim 1, wherein the received information includes one of (i) a message, (ii) a video, (iii) a uniform resource locator, and (iv) an image.

4. The method of claim 1, wherein the received information includes information that the second party is restricted from accessing based on one of (i) a time, (ii) a date, and (iii) a location of the second party.

5. The method of claim 1, further comprising receiving feedback from the device associated with the second party indicating (i) an acceptance of the modified behavioral expectation or (ii) a rejection of the modified behavioral expectation.

6. The method of claim 1, wherein the device associated with the first party is a robotic device that includes a mechanical actuator.

7. The method of claim 1, wherein the second party is connected to the first party by a symmetric connection, wherein the symmetric connection is formed when the second party agrees to connect to the first party.

8. The method of claim 1, wherein the stored behavioral expectation associated with the second party includes at least one of (i) an action, (ii) a spoken word, (iii) a written word, and (iv) a vocalization.

9. A system comprising:
   a robotic device having at least one mechanical actuator;
   a computing system including a computer-readable memory; and program instructions stored on the computer-readable memory and executable by at least one processor to cause the computing system to:

make a determination of whether a first party is connected to a second party by a social-network, wherein the social-network comprises a network of parties, including the first party associated with a first party device and the second party associated with a robotic device, wherein the first party and the second party are related via one or more relationships, the one or more relationships indicating a type of connection between the first party and the second party;

based on the determination, query a behavioral database to obtain a behavioral expectation associated with the first party, wherein the behavioral expectation indicates an action associated with the first party;

compare the behavioral expectation associated with the first party to a stored behavioral expectation associated with the second party to determine if the behavioral expectation associated with the first party is substantially different from the stored behavioral expectation associated with the second party; and responsive to the comparison, modify the stored behavioral expectation associated with the second party based on the behavioral expectation associated with the first party.

10. The system of claim 9, further comprising program instructions stored on the computer-readable memory and executable by the computing system to:

provide instructions, which are executable to perform an action associated with the modified behavioral expectation, to the robotic device associated with the second party.

11. The system of claim 10, wherein the first party device is a robotic device having a mechanical actuator.

12. The system of claim 9, further comprising program instructions stored on the computer-readable memory and executable by the computing system to:

restrict access to data associated with the second party based on at least one of (i) a time, (ii) a date, and (iii) a location of the first party.

13. The system of claim 9, wherein the first party is connected to the second party by an asymmetric connection, wherein the asymmetric connection is formed after a second party requests to connect to the first party.

14. A non-transitory computer-readable memory having stored thereon instructions executable by a computing device having at least one processor to cause the computing device to perform functions comprising:

receiving information associated with a first party, wherein the first party is connected to a second party by a social-network, wherein the second party is associated with a robotic device having a mechanical actuator, wherein the social-network comprises a network of parties, including the first party and the second party, that are related via one or more relationships, the one or more relationships indicating a type of connection between the first party and the second party;

based on the received information, querying a behavioral database to obtain a behavioral expectation associated with the first party, wherein the behavioral expectation indicates an action associated with the first party;

comparing the behavioral expectation associated with the first party to a stored behavioral expectation associated with the first party is substantially different from or substantially similar to the stored behavioral expectation associated with the second party;

responsive to the comparing, modifying the stored behavioral expectation associated with the second party based on the behavioral expectation associated with the first party; and providing instructions, which are executable to perform an action associated with the modified behavioral expectation, to the robotic device associated with the second party.

15. The non-transitory computer-readable memory of claim 14, further comprising instructions executable by the computing device to cause the computing device to perform functions comprising:

identifying at least one of (i) an action, (ii) a spoken word, (iii) a written word, and (iv) a vocalization, based on the behavioral expectation associated with the second party.

16. The non-transitory computer-readable memory of claim 14, wherein the instructions, which are executable to perform an action associated with the modified behavioral expectation, are associated with at least one of (i) the action, (ii) the spoken word, (iii) the written word, and (iv) the vocalization.

17. The non-transitory computer-readable memory of claim 14, further comprising instructions executable by the computing device to cause the computing device to perform functions comprising:

determining if the first party is connected to the second party by the social network by:
querying a database having social network data;
and determining if a symmetric connection or an asymmetric connection exists between the first party and the second party.

18. The non-transitory computer-readable memory of claim 14, wherein the received information associated with the first party includes a command from the device associated with the second party that instructs a device associated with the first party to perform an action.

19. The non-transitory computer readable memory of claim 18, wherein the device associated with the first party is a robotic device.

20. The non-transitory computer-readable memory of claim 14, further comprising instructions executable by the computing device to cause the computing device to perform functions comprising:

receiving feedback from the device associated with the first party indicating (i) an acceptance of the modified behavioral expectation or (ii) a rejection of the modified behavioral expectation.

* * * * *